United States Patent
Fischer et al.

(10) Patent No.: US 11,702,478 B2
(45) Date of Patent: Jul. 18, 2023

(54) AGONISTIC CD40 ANTIBODIES

(71) Applicant: MAB DISCOVERY GMBH, Neuried (DE)

(72) Inventors: Stephan Fischer, Weilheim (DE); Karsten Beckmann, Vaterstetten (DE)

(73) Assignee: MAB DISCOVERY GMBH, Neuried (DE)

( * ) Notice: Subject to any disclaimer, the term of this patent is extended or adjusted under 35 U.S.C. 154(b) by 163 days.

(21) Appl. No.: 16/648,731

(22) PCT Filed: Sep. 19, 2018

(86) PCT No.: PCT/EP2018/075388
§ 371 (c)(1),
(2) Date: Mar. 19, 2020

(87) PCT Pub. No.: WO2019/057792
PCT Pub. Date: Mar. 28, 2019

(65) Prior Publication Data
US 2020/0239583 A1 Jul. 30, 2020

(30) Foreign Application Priority Data
Sep. 19, 2017 (EP) .................................. 17191974

(51) Int. Cl.
*A61K 39/395* (2006.01)
*C07K 16/28* (2006.01)
(Continued)

(52) U.S. Cl.
CPC .......... *C07K 16/2878* (2013.01); *A61P 35/00* (2018.01); *A61K 2039/505* (2013.01); *C07K 2317/565* (2013.01); *C07K 2317/75* (2013.01)

(58) Field of Classification Search
None
See application file for complete search history.

(56) References Cited

U.S. PATENT DOCUMENTS 7,193,064 B2 * 3/2007 Mikayama .............. A61P 37/08
530/388.73
7,338,660 B2 3/2008 Bedian et al.
(Continued)

FOREIGN PATENT DOCUMENTS

EP 3401332 A1 11/2018
JP 2014515612 A 7/2014
(Continued)

OTHER PUBLICATIONS

The Human Protein Atlas (2022), CD40, Retrieved online: <URL:https://www.proteinatlas.org/ENSG00000101017-CD40m> [ retrieved on Mar. 4, 2022].*
(Continued)

*Primary Examiner* — Claire Kaufman
(74) *Attorney, Agent, or Firm* — Meunier Carlin & Curfman LLC

(57) ABSTRACT

The present invention relates to humanized monoclonal antibodies or antigen-binding fragments thereof that specifically bind to human CD40 receptor and induce CD40 signaling independent of Fcy mediated CD40 receptor cross-linking. The antibodies of the present invention bind to a CD40 epitope that overlaps with the epitope of the CD40 ligand and can activate human APCs. The present invention also provides for compositions comprising said antibodies and uses for the antibodies and compositions in the treatment of patients suffering from cancer.

Figures 7, 8:
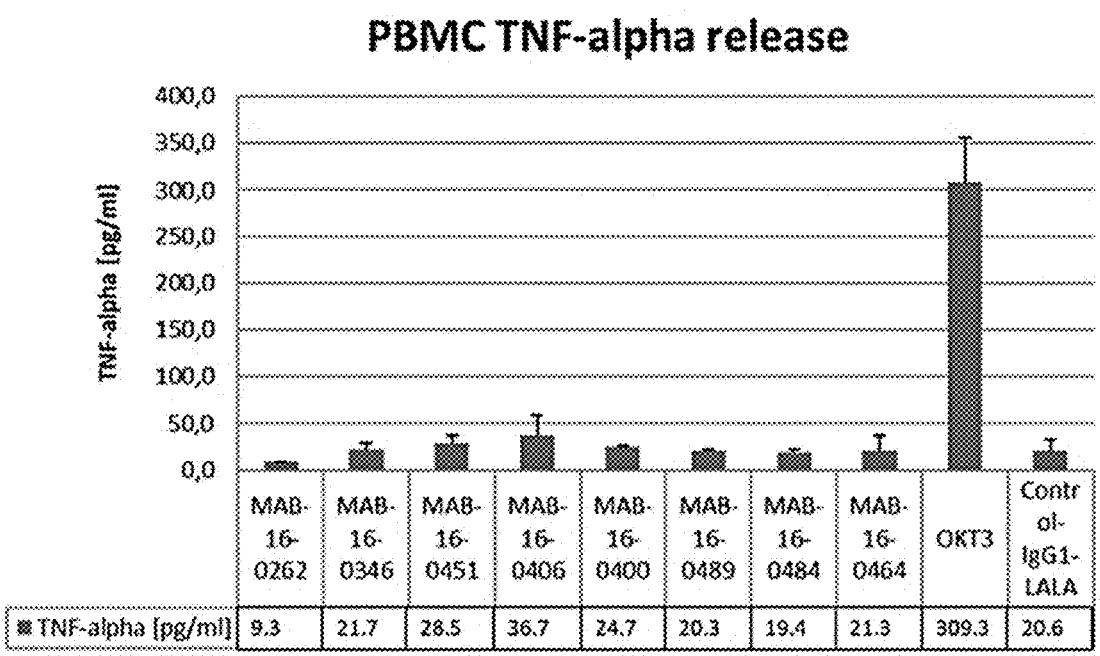

13 Claims, 27 Drawing Sheets
Specification includes a Sequence Listing.

(51) Int. Cl.
*A61P 35/00* (2006.01)
*A61K 39/00* (2006.01)

(56) References Cited

U.S. PATENT DOCUMENTS

| | | | |
|---|---|---|---|
| 11,084,882 B2* | 8/2021 | Altintas | C07K 16/2878 |
| 2006/0062784 A1 | 3/2006 | Grant et al. | |
| 2006/0093600 A1 | 5/2006 | Bedian et al. | |
| 2012/0121585 A1 | 5/2012 | Heusser et al. | |
| 2017/0088624 A1 | 3/2017 | Fransson et al. | |

FOREIGN PATENT DOCUMENTS

| | | | |
|---|---|---|---|
| JP | 2017511379 A | 4/2017 | |
| JP | 2019521645 A | 8/2019 | |
| WO | 2012149356 A2 | 11/2012 | |
| WO | 2013/034904 A1 | 3/2013 | |
| WO | 2015145360 A1 | 10/2015 | |
| WO | 2017/004016 A1 | 1/2017 | |
| WO | 2017009473 A1 | 1/2017 | |
| WO | 2017184619 A2 | 10/2017 | |

OTHER PUBLICATIONS

MacCallum et al., Antibody-antigen interactions: contact analysis and binding site topography, J. Mol. Biol. 262:732-745, 1996.*
NCI Diectionaries (2022), CD40 agonist monolconal antibody CP-870,893, Retrieved online: <URL:https://www.cancer.gov/publications/dictionaries/cancer-drug/def/cd40-agonist-monoclonal-antibody-cp-870893> [retrieved on Mar. 4, 2022].*
Schlothauer et al., Novel human IgG1 and IgG4 Fc-engineered antibodies with completely abolished immune effector functions, Prot. Eng. Design Selection, 29(10):457-466, 2016.*
Lamminmaki et al., Crystal structure of a recombinant anti-estradiol Fab fragment in complex with 17/3-estradiol, J. Biol. Chem. 276 (39):36687-36694, 2001.*
Chen et al., Enhancement and destruction of antibody function by somatic mutation: unequal occurrence is controlled by V gene combinatorial associations, EMBO J. 14(12):2784-2794, 1995.*
Nezlin, RS, Biochemistry of Antibodies, Plenum Press:New York, p. 160, 1970.*
Kranz et al., Restricted reassociation of heavy and light chains from hapten-specific monoclonal antibodies, Proc. Natl. Acad. Sci. USA 78(9):5807-5811, 1981.*
Vonderheide et al., Clinical activity and immune modulation in cancer patients treated with CP-870,893, a novel CD40 agonist monoclonal antibody, J. Clin. Oncol. 25(7):876-883, 2007.*
Herold et al., Determinants of the assembly and function of antibody variable domains Scientific Reports, 7:12276, DOI:10.1038/s41598-017-12519-9, Sep. 2017.*
Office Action issued in the corresponding Singapore application No. 11202002366V dated Sep. 13, 2021.
L.P. Rich et al: "Role of Crosslinking for Agnostic CD40 Monoclonal Antibodies as Immune Therapy of Cancer", Cancer Immunology Research, vol. 2, No. 1, Jan. 1, 2014, pp. 19-26. XP055393427.
Dahan Rony et al: "Therapeutic Activity of Agonistic, Human AntiCD40 Monoclonal Antibodies Requires Selective Fc[gamma]R Engagement", Cancer Cell, Cell Press, US, vol. 29, No. 6, Jun. 2, 2016 (Jun. 2, 2016), pp. 820-831, XP029601430.
Ann L. White et al: "Conformation of the Human Immunoglobulin G2 Hinge Imparts Superagonistic Properties to Immunostimulatory Anticancer Antibodies", Cancer Cell, vol. 27, No. 1, Jan. 1, 2015 (Jan. 1, 2015), pp. 138-148, XP055193819.
International Search Report and Written Opinion in PCT/EP2018/075388. dated Feb. 14, 2019. 23 pages.
White, A. L., et al., "Fcγ Receptor Dependency of Agonistic CD40 Antibody in Lymphoma Therapy Can Be Overcome through Antibody Multimerization," The Journal of Immunology, vol. 193, No. 4, 2014, pp. 1828-1835.
Notice of Reasons for Refusal, dated Aug. 16, 2022, received in corresponding JP Patent Application No. 2020-515887 (and English translation).

* cited by examiner

Fig.1:

| Antibody | Cell binding EC50 [ng/ml] |
|---|---|
| MAB-16-0262 | 6.3 |
| MAB-16-0346 | 49.5 |
| MAB-16-0451 | 8.9 |
| MAB-16-0489 | 3.2 |
| MAB-16-0484 | 21.9 |
| MAB-16-0464 | 3.0 |
| MAB-16-0267 | 3.4 |
| MAB-16-0406 | 6.6 |
| MAB-16-0400 | 5.8 |
| CP-870-IgG1-LALA | 14.5 |

Fig. 2:

| Antibody | HEK-Blue™ EC50 [ng/ml] |
|---|---|
| MAB-16-0262 | 1957 |
| MAB-16-0346 | 6243 |
| MAB-16-0406 | 1235 |
| MAB-16-0400 | 2168 |
| MAB-16-0451 | 2267 |
| MAB-16-0489 | 1127 |
| MAB-16-0464 | 1437 |
| MAB-16-0267 | 2333 |
| MAB-16-0283 | 1445 |
| MAB-16-0325 | 2211 |
| MAB-16-0377 | 900 |
| MAB-16-0386 | 1386 |
| MAB-16-0388 | 576 |

Fig. 3:

| Antibody | OD at 450 nm |
|---|---|
| MAB-16-0262 | 0.11 |
| MAB-16-0346 | 0.09 |
| MAB-16-0451 | 0.13 |
| MAB-16-0489 | 0.01 |
| MAB-16-0484 | 0.07 |
| MAB-16-0464 | 0.09 |
| MAB-16-0267 | 0.10 |
| MAB-16-0406 | 0.07 |
| MAB-16-0400 | 0.08 |
| CP-870-IgG1-LALA | 2.54 |

Fig. 4:

| Antibody | Cyno-CD40 ELISA EC50 [ng/ml] |
|---|---|
| MAB-16-0262 | 11.9 |
| MAB-16-0346 | 8.2 |
| MAB-16-0451 | 10.4 |
| MAB-16-0484 | 31.8 |
| MAB-16-0464 | 8 |
| MAB-16-0267 | 7 |
| MAB-16-0406 | 11.1 |
| CP-870.893 | 8 |

Fig. 5 a):

| Antibody | IL12p40 [ng/ml] |
|---|---|
| MAB-16-0262 | >24.0 |
| MAB-16-0267 | 1.9 |
| MAB-16-0283 | 1.7 |
| MAB-16-0346 | 9.5 |
| MAB-16-0325 | 1.2 |
| MAB-16-0377 | 0.8 |
| MAB-16-0386 | 0.9 |
| MAB-16-0388 | 0.9 |
| MAB-16-0406 | 17.0 |
| MAB-16-0400 | 11.1 |
| MAB-16-0451 | >24.0 |
| MAB-16-0489 | 8.3 |
| MAB-16-0484 | 4.6 |
| MAB-16-0464 | >24.0 |
| IgG1-LALA control | 0 |

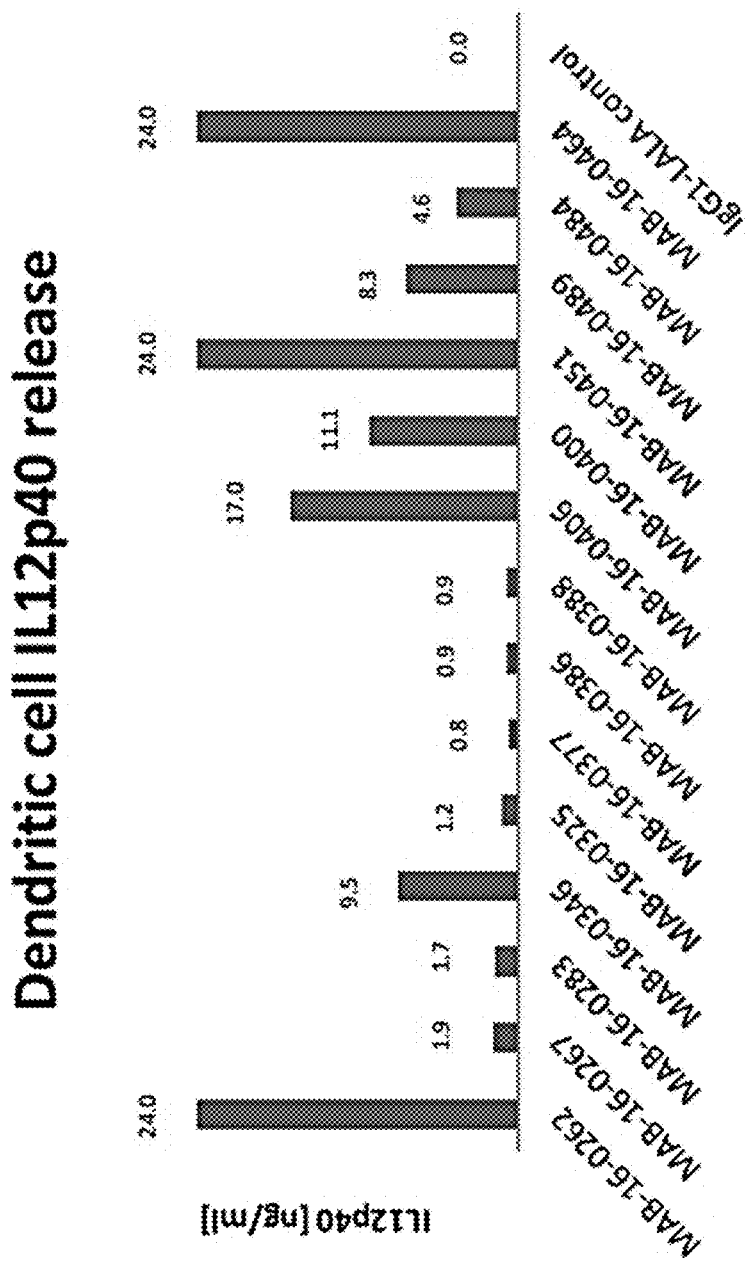
Fig. 5 b): Continued

Fig. 6:

|  | Secreted IL-12p40 by anti-CD40 treated dendritic cells [ng/ml] | | | |
|---|---|---|---|---|
| Antibody | 5µg/ml antibody | 1.7µg/ml antibody | 0.6µg/ml antibody | 0.2µg/ml antibody |
| MAB-16-0262 | 55.2 | 81.5 | 81.8 | 35.8 |
| MAB-16-0451 | 81.7 | 207.7 | 164.0 | 57.9 |
| MAB-16-0489 | 13.4 | 17.7 | 10.3 | 2.8 |
| MAB-16-0484 | 6.8 | 7.8 | 3.5 | 0 |
| MAB-16-0267 | 2.5 | 2.6 | 2.1 | 0 |
| MAB-16-0406 | 19.4 | 34.7 | 24.7 | 11.8 |
| CP870-IgG1-LALA | 1.6 | 2.1 | 1.2 | 0.7 |
| CP870-IgG1-V11 | 76.1 | 72.2 | 77.5 | 26.1 |
| CP870-IgG2 | 5.7 | 5.8 | 0 | 0 |
| CP870-IgG1 | 32.0 | 31.5 | 0 | 0 |
| Control IgG1-LALA | 0 | 0 | 0 | 0 |

| Antibody | IL12p40 release EC50 [ng/ml] |
|---|---|
| MAB-16-0262 | 416 |
| MAB-16-0406 | 380 |
| MAB-16-0400 | 392 |
| MAB-16-0451 | 659 |
| MAB-16-0489 | 743 |
| MAB-16-0484 | 388 |

Fig. 11:

| Experiment | | HLA-DR | CD86 | CD80 | CD83 | CD54 | CD95 |
|---|---|---|---|---|---|---|---|
| | | \multicolumn{6}{c|}{FACS Coreceptor analysis (FOI over isotype antibody treatment} |
| Donor 1 | CP870IgG1LALA | 1.3 | 1.3 | 1.1 | n.a. | n.a. | n.a. |
| | CP870IgG2 | 6.1 | 3.9 | 1.9 | n.a. | n.a. | n.a. |
| | MAB-16-0451 | 11.5 | 16.6 | 3.8 | n.a. | n.a. | n.a. |
| | MAB-16-0262 | 10.7 | 13.0 | 3.2 | n.a. | n.a. | n.a. |
| | MAB-16-0464 | 10.9 | 7.5 | 2.4 | n.a. | n.a. | n.a. |
| | MAB-16-0406 | 8.3 | 7.5 | 1.9 | n.a. | n.a. | n.a. |
| | MAB-16-0267 | 1.0 | 1.2 | 1.0 | n.a. | n.a. | n.a. |
| | CD40L | 8.8 | 7.4 | 1.8 | n.a. | n.a. | n.a. |
| Donor 2 | CP870IgG2 | 5.5 | 5.7 | 2.2 | 7.4 | n.a. | n.a. |
| | MAB-16-0451 | 5.5 | 9.9 | 3.5 | 5.8 | n.a. | n.a. |
| | MAB-16-0262 | 6.2 | 11.4 | 3.7 | 7.4 | n.a. | n.a. |
| | MAB-16-0464 | 7.2 | 9.6 | 2.8 | 7.4 | n.a. | n.a. |
| | MAB-16-0406 | 6.3 | 8.2 | 2.2 | 6.5 | n.a. | n.a. |
| | MAB-16-0267 | 0.8 | 0.9 | 0.8 | 0.7 | n.a. | n.a. |
| Donor 3 | CP870IgG1LALA | 2.2 | 2.8 | 1.4 | 2.4 | 1.8 | 1.2 |
| | CP870IgG2 | 3.6 | 7.5 | 2.0 | 4.4 | 3.0 | 1.4 |
| | MAB-16-0451 | 3.4 | 19.3 | 4.1 | 4.2 | 1.9 | 1.5 |
| | MAB-16-0262 | 3.2 | 17.2 | 3.5 | 4.6 | 2.7 | 1.5 |
| | MAB-16-0464 | 4.2 | 16.3 | 3.2 | 4.2 | 2.5 | 1.5 |
| | MAB-16-0406 | 3.0 | 12.2 | 2.7 | 4.0 | 2.1 | 1.5 |
| | MAB-16-0267 | 1.3 | 1.6 | 1.3 | 1.2 | 1.2 | 1.1 |

Fig. 12:

| Experiment | | ELISA [ng/ml] | | Cytometric bead array [ng/ml] | | | | |
|---|---|---|---|---|---|---|---|---|
| | | IL12p40 | IL12p70 | IL1b | IL-6 | IL-10 | TNF-a | IL-8 |
| Donor 1 | CP870IgG1LALA | 0.0 | 40.5 | 1.7 | 0.3 | 0.3 | 0.0 | 0.1 |
| | CP870IgG2 | 11.3 | 60.4 | 1.6 | 0.2 | 0.0 | 0.2 | 0.0 |
| | MAB-16-0451 | 124.3 | 464.1 | 26.9 | 2.9 | 7.4 | 17.6 | 0.2 |
| | MAB-16-0262 | 87.4 | 277.4 | 10.0 | 1.3 | 2.6 | 4.9 | 0.1 |
| | MAB-16-0464 | 67.2 | 202.5 | 5.7 | 0.7 | 0.8 | 2.3 | 0.1 |
| | MAB-16-0406 | 33.1 | 232.5 | 3.6 | 0.8 | 0.9 | 0.3 | 0.1 |
| | MAB-16-0267 | 0.0 | 43.7 | 2.3 | 0.1 | 0.1 | 0.0 | 0.1 |
| | CD40L | 0.0 | 78.8 | 1.4 | 0.2 | 0.1 | 0.0 | 0.0 |
| | Control-IgG1-LALA | | 16.7 | 2.1 | 0.1 | 0.0 | 0.0 | 0.1 |
| Donor 2 | CP870IgG2 | 9.6 | 6.8 | 0.1 | 0.0 | 0.0 | 0.1 | 0.0 |
| | MAB-16-0451 | 256.3 | 124.7 | 11.6 | 0.1 | 3.5 | 13.0 | 0.0 |
| | MAB-16-0262 | 124.8 | 80.3 | 6.3 | 0.0 | 1.5 | 5.2 | 0.0 |
| | MAB-16-0464 | 55.2 | 28.2 | 1.2 | 0.0 | 0.1 | 0.0 | 0.0 |
| | MAB-16-0406 | 16.1 | 24.2 | 0.4 | 0.0 | 0.0 | 0.0 | 0.0 |
| | MAB-16-0267 | 0.0 | 0.9 | 0.0 | 0.0 | 0.0 | 0.0 | 0.0 |
| | Control-IgG1-LALA | 0.8 | 1.3 | 0.0 | 0.0 | 0.1 | 0.0 | 0.0 |
| Donor 3 | CP870IgG1LALA | 10.8 | 9.9 | 0.1 | 0.1 | 0.0 | 0.0 | 0.0 |
| | CP870IgG2 | | 10.1 | 3.9 | 0.1 | 1.1 | 3.2 | 0.0 |
| | MAB-16-0451 | 135.9 | 139.2 | 2.7 | 0.1 | 0.5 | 1.2 | 0.0 |
| | MAB-16-0262 | 102.1 | 89.5 | 0.4 | 0.0 | 0.1 | 0.1 | 0.0 |
| | MAB-16-0464 | 30.1 | 32.3 | 0.1 | 0.0 | 0.0 | 0.0 | 0.0 |
| | MAB-16-0406 | 9.6 | 26.9 | 0.0 | 0.0 | 0.0 | 0.0 | 0.0 |
| | MAB-16-0267 | 0.0 | 6.0 | 0.0 | 0.0 | 0.0 | 0.0 | 0.0 |
| | Control-IgG1-LALA | | 3.3 | 0.0 | 0.0 | 0.0 | 0.0 | 0.0 |

| | Cytometric bead array [EC50 in ng/ml] | | | | | |
|---|---|---|---|---|---|---|
| Antibody | IL12p70 | IL-1b | IL-6 | IL-10 | TNF-a | IL-8 |
| CP870 IgG2 | 213 | 263 | n.d. | n.d. | 244 | n.d. |
| MAB-16-0451 | 146 | 287 | 185 | 215 | 280 | n.d. |
| MAB-16-0262 | 189 | 294 | 213 | 285 | 289 | n.d. |
| MAB-16-0464 | 156 | 183 | n.d. | 172 | 169 | n.d. |
| MAB-16-0406 | 208 | 192 | 320 | 189 | 239 | n.d. |
| MAB-16-0267 | n.d. | n.d. | n.d. | n.d. | n.d. | n.d. |

| Antibody | FACS Coreceptor analysis EC50 [ng/ml] | | |
|---|---|---|---|
| | HLA-DR | CD86 | CD80 |
| CP870 IgG2 | 8 | 12 | n.a. |
| MAB-16-0451 | 5 | 5 | 11 |
| MAB-16-0262 | 18 | 18 | n.a. |
| MAB-16-0464 | n.a. | n.a. | n.a. |
| MAB-16-0406 | n.a. | n.a. | n.a. |
| MAB-16-0267 | n.a. | n.a. | n.a. |

Fig.18:

|  | $K_D$ (nM) |
|---|---|
| Ab MAB-16-0262/human CD40 | 15.7 ± 1.1 |
| Ab MAB-16-0451/human CD40 | 1.2 ± 0.0 |
| Ab MAB-16-0464/human CD40 | 2.6 ± 0.0 |
| CP-870.893/human CD40 | 8.9 ± 1.4 |
| Ab MAB-16-0262/cyno CD40 | 10.3 ± 0.2 |
| Ab MAB-16-0451/cyno CD40 | 0.8 ± 0.0 |
| Ab MAB-16-0464/cyno CD40 | 2.2 ± 0.1 |

Fig.21:

| Antibody | Mouse | Body temp. at day 3 [ºC] | Survival at day 3 |
|---|---|---|---|
| CP-870.893 | 1 | 31.3 | - |
| | 2 | 34.8 | + |
| | 3 | 35.5 | + |
| | 4 | 32.3 | - |
| | 5 | 32.6 | - |
| | 6 | 35.5 | + |
| hIgG2 | 1 | 35.8 | + |
| | 2 | 35.5 | + |

| Antibody | Mouse | Body temp. at day 4 [ºC] | Survival at day 4-24 |
|---|---|---|---|
| MAB-16-0451 | 1 | 36.9 | + |
| | 2 | 36.6 | + |
| | 3 | 36.2 | + |
| hIgG1 | 1 | 37.0 | + |

Fig.22 a:	Sequences (amino acids in one letter code)

Complete sequences of Variable Regions (VR):

Heavy chain:	VH complete:	SEQ ID NO: 1-14
Light chain:	VL complete:	SEQ ID NO: 15-28

| mAB name | SEQ ID NO. | Complete Heavy-chain VR sequence |
|---|---|---|
| MAB-16-0283 | 1 | EVQLEESGGDLVQPGASLRLSCAASGFSFSFSYWICWVRQAPGKGLELVSCIYTTSGSTYYASWAKGRFTISIDNSKTTLYLQMNSLRAEDTATYFCARSSGVSYPSYFHLWGQGTLVTVSS |
| MAB-16-0377 | 2 | EVQLEESGGGLVQPGASLRLSCAASGFSFSGYWMCWVRQAPGKGLEWVGCIYTNSGVTYYANWAKGRFTISKDTSKTTLYLQMNSLRAEDTATYFCARGGAIYNDYDYAFYYSLWGQGTLVTVSS |
| MAB-16-0267 | 3 | EVQLEESGGDLVQPGASLRLSCAASGFDFNSNAMSWVRQAPGKGLEWVASIYAGGSGSTYYASWAKGRFTISKDTSKTTLYLQMNSLRAEDTATYFCARGITRLPLWGQGTLVTVSS |
| MAB-16-0386 | 4 | EVQLEESGGDLVQPGASLRLSCAVSGFDFSSNAMSWVRQAPGKGLEWVSSIYAGSSGSTYYASWAKGRFTISKDASKTTLYLQMNSLRAEDTATYFCARGVTRLPLWGQGTLVTVSS |
| MAB-16-0451 | 5 | EVQLEESGGGLVQPGGSLRLSCAASGFDFSSNTMCWVRQAPGKGLEWVACIYAGSSGSTYYASWAKGRFTISKDISKTTLYLQMNSLRAEDTATYFCARGLSRFSLWGQGTLVTVSS |
| MAB-16-0346 | 6 | EVQLEESGGGLVQPGGSLRLSCAASGFDFSTNAVSWVRQAPGKGLEWVGSISAGSSGSTYYASWAKGRFTISKDTSKTTLYLQMNSLRAEDTATYFCARGYTYLTLWGQGTLVTVSS |
| MAB-16-0325 | 7 | EVQLEESGGGLVQPGGSLRLSCAASGFSFSSNAMSWVRQAPGKGPEWVVTIYAGSSGSTYYASWAKGRFTISKDTSKTTLYLQMNSLRAEDTATYFCARGATYLTLWGQGTLVTVSS |
| MAB-16-0388 | 8 | EVQLVESGGGLVQPGGSLRLSCAASGFDFSSNAMSWVRQAPGKGLEWVGIIYAGSSGSTYYASWAKGRFTISKDTSKTTLYLQMNSLRAEDTATYFCARGATYITLWGQGTLVTVSS |
| MAB-16-0464 | 9 | EVQLEESGGGLVQPGGSLRLSCAASGFDFSSNAMSWVRQAPGKGLEWVGTIYAGSNGNTDYASWAKGRFTISKDTSKTTLYLQMNSLRAEDTATYFCARGASYFTLWGQGTLVTVSS |
| MAB-16-0262 | 10 | EVQLEESGGGLVQPGGSLRLSCAASGFDFSTNAMCWVRQAPGKGLEWVACIAAGSSIITYYASWAKGRFTISKDTSKTTLYLQMNSLRAEDTAVYFCARGLSRFALWGQGTLVTVSS |
| MAB-16-0406 | 11 | EVQLEESGGGLVQPGGSLRLSCAASGIDFSRYYMCWVRQAPGKGPEWVACYSNGDGSTYYASWAKGRFTISKDTSKTTLYLQMNSLRAEDTATYFCARGADYSAGAAAFNLWGQGTLVTVSS |
| MAB-16-0484 | 12 | EVQLEESGGGLVQPGGSLRLSCAASGIDFSRYYYICWVRQAPGKGPEWVACFANGDGSTYYASWAKGRFTISKDTSKTTLYLQMNSLRAEDTATYFCARGADYSGGAAAFNLWGQGTLVTVSS |
| MAB-16-0400 | 13 | EVQLEESGGGLVQPGGSLRLSCAASGIDFSRYFYMCWVRQAPGKGLEWVACIGPGVSGDTYYASWAKGRFTISGDTSKTTLYLQMNSLRAEDTATYFCARGVDYTYGDAGAAFNLWGQGTLVTVSS |
| MAB-16-0489 | 14 | EVQLEESGGGLVQPGASLRLSCAASGIDFSRYFYVCWVRQAPGKGLEWVGCFANHDDSIYYAGWMNGRFTISKDTSKTTLYLQMNSLRAEDTATYFCARGVDYTVGYGGAAFNLWGQGTLVTVSS |

Continued

Fig.22 b:

| mAB name | SEQ ID NO. | Complete k-Light chain VR sequence |
|---|---|---|
| MAB-16-0283 | 15 | DIQMTQSPSSLSASVGDRVTITCQASQSISSYLAWYQQKPGQAPKLLIYSASKLPSGVPSRFSGSGSGTDFTLTISSLQPEDFATYHCQTYYYSSSSSYDYGFGQGTKVVIK |
| MAB-16-0377 | 16 | DIVMTQSPSSLSASVGDRVTITCQASQSISSYLAWYQQKPGQAPKLLIYKASTLASGVPSRFSGSGSGTDFTLTISSLQPEDFATYYCQSYYGSSSISYNAFGQGTKVVIK |
| MAB-16-0267 | 17 | DIQMTQSPSSLSASVGDRVTITCQASQSISSYLAWYQQKPGQAPKLLIYDASKLASGVPSRFSGSGSGTDFTLTISSLQPEDFATYYCQGTYYGSTTISAFGQGTKVVIK |
| MAB-16-0386 | 18 | DIVMTQSPSSLSASVGDRVTITCQASQSISSYLAWYQQKPGQAPKLLIYDASTLASGVPSRFSGSGSGTDFTLTISSLQPEDFATYYCQGTVYGSSTISAFGQGTKVVIK |
| MAB-16-0451 | 19 | DIVMTQSPSSLSASVGDRVTITCQASQSISNYLAWYQQKPGQAPKLLIYDASKLASGVPSRFSGSGSGTDFTLTISSLQPEDFATYYCQGGDYYGSSYVVAFGGGTKVVIK |
| MAB-16-0346 | 20 | DIVMTQSPSSLSASVGDRVTITCQASHSISSTYLSWYQQKPGQAPKLLIYRASTLASGVPSRFSGSGSGTDFTLTISSLQPEDFATYYCQYTDYGSSYVSTFGQGTKVVIK |
| MAB-16-0325 | 21 | DIVMTQSPSSLSASVGDRVTITCQASQSISNYLSWYQQKPGQAPKLLIYRASTLPSGVPSRFSGSGSGTDFTLTISSLQPEDFATYYCQGYYYSGTTYDSTAFGQGTKVVIK |
| MAB-16-0388 | 22 | DIVMTQSPSSLSASVGDRVTITCQASQSIGSYLAWYQQKPGQAPKLLIYRASTLASGVPSRFSGSGSGTDFTLTISSLQPEDFATYYCQGYYYSTTTTTYDSSAFGQGTKVVIK |
| MAB-16-0464 | 23 | DIVMTQSPSSLSASVGDRVTITCQASESVVSNNRLAWYQQKPGQAPKLLIYLASTLPSGVPSRFSGSGSGTDFTLTISSLQPEDFATYYCAGYKSSTDGTAFGQGTKVVIK |
| MAB-16-0262 | 24 | DIVMTQSPSSLSASVGDRVTITCQASQSISSYLSWYQQKPGQAPKLLIYLTSTLASGVPSRFSGSGSGTDFTLTISSLQPEDFATYYCQGYYSSSSYVSNGFGQGTKVVIK |
| MAB-16-0406 | 25 | DIQMTQSPSSLSASVGDRVTITCQASESIGNALVWYQQKPGQAPKLLIYRASILASGVPSRFSGSGSGTDFTLTISSLQPEDFATYYCQDYYGSSTEYNTFGQGTKVVIK |
| MAB-16-0484 | 26 | DIQMTQSPSSLSASVGDRVTITCQASQSISSRLAWYQQKPGQAPKLLIYRASTLASGVPSRFSGSGSGTDFTLTISSLQPEDFATYYCQDYYGSSTEYNAFGQGTKVVIK |
| MAB-16-0400 | 27 | DIVMTQSPSSLSASVGDRVTITCQASQSISSYLAWYQQKPGQAPKLLIYRASILASGVPSRFSGSGSGTDFTLTISSLQPEDFATYYCQTYYSSRTYSYGSPNAFGQGTKVVIK |
| MAB-16-0489 | 28 | DIVMTQSPSSLSASVGDRVTITCQASQSIGSYLSWYQQKPGQAPKLLIYRATTLASGVPSRFSGSGSGTDFTLTISSLQPEDFATYYCQSYYRDSSSSAFGQGTKVVIK |

Continued

Fig.22 c:

Complementary Determining Regions (CDR):

Heavy Chain:         CDR-H1:         SEQ ID NO: 29-42
                           CDR-H2:         SEQ ID NO: 43-56
                           CDR-H3:         SEQ ID NO: 57-70

| mAB name | SEQ ID NO. | CDR_H1 sequence |
|---|---|---|
| MAB-16-0283 | 29 | FSYWIC |
| MAB-16-0377 | 30 | GYWMC |
| MAB-16-0267 | 31 | SNAMS |
| MAB-16-0386 | 32 | SNAMS |
| MAB-16-0451 | 33 | SNTMC |
| MAB-16-0346 | 34 | TNAVS |
| MAB-16-0325 | 35 | SNAMS |
| MAB-16-0388 | 36 | SNAMS |
| MAB-16-0464 | 37 | SNAMS |
| MAB-16-0262 | 38 | TNAMC |
| MAB-16-0406 | 39 | RYYYMC |
| MAB-16-0484 | 40 | RYYYIC |
| MAB-16-0400 | 41 | RYFYMC |
| MAB-16-0489 | 42 | RYFYVC |

Continued

Fig.22 d:

| mAB name | SEQ ID NO. | CDR_H2 sequence |
|---|---|---|
| MAB-16-0283 | 43 | CIYTTSGSTYYASWAKG |
| MAB-16-0377 | 44 | CIYTNSGVTYYANWAKG |
| MAB-16-0267 | 45 | SIYAGGSGSTYYASWAKG |
| MAB-16-0386 | 46 | SIYAGSSGSTYYASWAKG |
| MAB-16-0451 | 47 | CIYAGSSGSTYYASWAKG |
| MAB-16-0346 | 48 | SISAGSSGSTYYASWAKG |
| MAB-16-0325 | 49 | TIYAGSSGSTYYASWAKG |
| MAB-16-0388 | 50 | IIYAGSSGSTYYASWAKG |
| MAB-16-0464 | 51 | TIYAGSNGNTDYASWAKG |
| MAB-16-0262 | 52 | CIAAGSSIITYYASWAKG |
| MAB-16-0406 | 53 | CYSNGDGSTYYASWAKG |
| MAB-16-0484 | 54 | CFANGDGSTYYASWAKG |
| MAB-16-0400 | 55 | CIGPGVSGDTYYASWAKG |
| MAB-16-0489 | 56 | CFANHDDSIYYAGWMNG |

Continued

Fig.22 e:

| mAB name | SEQ ID NO. | CDR_H3 sequence |
|---|---|---|
| MAB-16-0283 | 57 | SSGVSYPSYFHL |
| MAB-16-0377 | 58 | GGAIYNDYDYAFYYSL |
| MAB-16-0267 | 59 | GITRLPL |
| MAB-16-0386 | 60 | GVTRLPL |
| MAB-16-0451 | 61 | GLSRFSL |
| MAB-16-0346 | 62 | GYTYLTL |
| MAB-16-0325 | 63 | GATYLTL |
| MAB-16-0388 | 64 | GATYITL |
| MAB-16-0464 | 65 | GASYFTL |
| MAB-16-0262 | 66 | GLSRFAL |
| MAB-16-0406 | 67 | GADYSAGAAAFNL |
| MAB-16-0484 | 68 | GADYSGGAAAFNL |
| MAB-16-0400 | 69 | GVDYTYGDAGAAFNL |
| MAB-16-0489 | 70 | GVDYTVGYGGAAFNL |

Continued

Fig.22 f:

Light Chain:     CDR-L1:     SEQ ID NO: 71-84
                 CDR-L2:     SEQ ID NO: 85-98
                 CDR-L3:     SEQ ID NO: 99-112

| mAB name | SEQ ID NO. | CDR_L1 sequence |
|---|---|---|
| MAB-16-0283 | 71 | QASQSISSYLA |
| MAB-16-0377 | 72 | QASQSISSYLA |
| MAB-16-0267 | 73 | QASQSISSYLA |
| MAB-16-0386 | 74 | QASQSISSYLA |
| MAB-16-0451 | 75 | QASQSISNYLA |
| MAB-16-0346 | 76 | QASHSISSTYLS |
| MAB-16-0325 | 77 | QASQSISNYLS |
| MAB-16-0388 | 78 | QASQSIGSYLA |
| MAB-16-0464 | 79 | QASESVVSNNRLA |
| MAB-16-0262 | 80 | QASQSISSYLS |
| MAB-16-0406 | 81 | QASESIGNALV |
| MAB-16-0484 | 82 | QASQSISSRLA |
| MAB-16-0400 | 83 | QASQSISSYLA |
| MAB-16-0489 | 84 | QASQSIGSYLS |

Continued

Fig.22 g:

| mAB name | SEQ ID NO. | CDR_L2 sequence |
|---|---|---|
| MAB-16-0283 | 85 | SASKLPS |
| MAB-16-0377 | 86 | KASTLAS |
| MAB-16-0267 | 87 | DASKLAS |
| MAB-16-0386 | 88 | DASTLAS |
| MAB-16-0451 | 89 | DASKLAS |
| MAB-16-0346 | 90 | RASTLAS |
| MAB-16-0325 | 91 | RASTLPS |
| MAB-16-0388 | 92 | RASTLAS |
| MAB-16-0464 | 93 | LASTLPS |
| MAB-16-0262 | 94 | LTSTLAS |
| MAB-16-0406 | 95 | RASILAS |
| MAB-16-0484 | 96 | RASTLAS |
| MAB-16-0400 | 97 | RASILAS |
| MAB-16-0489 | 98 | RATTLAS |

Continued

Fig.22 h:

| mAB name | SEQ ID NO. | CDR_L3 sequence |
|---|---|---|
| MAB-16-0283 | 99 | QTYYYSSSSSYDYG |
| MAB-16-0377 | 100 | QSYYGSSSISYNA |
| MAB-16-0267 | 101 | QGTYYGSTTISA |
| MAB-16-0386 | 102 | QGTVYGSSTISA |
| MAB-16-0451 | 103 | QGGDYYGSSYVVA |
| MAB-16-0346 | 104 | QYTDYGSSYVST |
| MAB-16-0325 | 105 | QGYYYSGTTYDSTA |
| MAB-16-0388 | 106 | QGYYSTTTTTYDSSA |
| MAB-16-0464 | 107 | AGYKSSSTDGTA |
| MAB-16-0262 | 108 | QGYYSSSSYVSNG |
| MAB-16-0406 | 109 | QDYYGSSTEYNT |
| MAB-16-0484 | 110 | QDYYGSSTEYNA |
| MAB-16-0400 | 111 | QTYYSSRTYSYGSPNA |
| MAB-16-0489 | 112 | QSYYRDSSSSA |

AGONISTIC CD40 ANTIBODIES

CROSS REFERENCE TO RELATED APPLICATIONS

This application claims priority to and is a United States National Phase Patent Application of International Patent Application Number PCT/EP2018/075388, filed on Sep. 19, 2018, which claims priority to EP Patent Application No. 17191974.9, filed on Sep. 19, 2017, both of which are incorporated by reference herein.

The attached "Sequence Listing" in TXT format entitled "10593_037USI_SequenceListing.TXT," created on Aug. 11, 2022, and 49,343 bytes in size, has been submitted in computer readable form and in compliance with 37 C.F.R. §§ 1.821-1.825, and is hereby incorporated by reference in its entirety.

FIELD OF INVENTION

The present invention relates to humanized monoclonal agonistic antibodies or antigen-binding fragments thereof that specifically bind to human CD40 receptor and are capable of inducing CD 40 signaling independent of Fcγ mediated CD40 receptor crosslinking. The invention also relates to uses of said antibodies and pharmaceutical compositions comprising them.

BACKGROUND

Recent success in cancer immunotherapy has revived the hypothesis that the immune system can control many if not most cancers, in some cases producing durable responses in a way not seen with many small-molecule drugs. Agonistic CD40 monoclonal antibodies (mAb) offer a new therapeutic option which has the potential to generate anticancer immunity by various mechanisms.

CD40 is a cell-surface molecule and a member of the tumor necrosis factor (TNF) receptor superfamily. It is expressed broadly on antigen-presenting cells (APC) such as dendritic cells, B cells, and monocytes as well as many nonimmune cells and in a range of tumors.

The natural ligand for CD40 is CD154, which is expressed primarily on the surface of activated T lymphocytes and provides a major component of T-cell "help" for immune responses: Signaling via CD40 on APC mediates, in large part, the capacity of helper T cells to license APC. Ligation of CD40 on DC, for example, induces increased surface expression of costimulatory and MHC molecules, production of proinflammatory cytokines, and enhanced T-cell triggering. CD40 ligation on resting B cells increases antigen-presenting function and proliferation.

The consequences of CD40 signaling are multifaceted and depend on the type of cell expressing CD40 and the microenvironment in which the CD40 signal is provided. Like some other members of the TNF receptor family, CD40 signaling is mediated by adapter molecules rather than by inherent signal transduction activity of the CD40 cytoplasmic tail. Downstream kinases are activated when the receptor is assembled, a multicomponent signaling complex translocates from CD40 to the cytosol and several well-characterized signal transduction pathways are activated.

Antagonizing human CD40 antibodies are known in the prior art. Respective antagonistic antibodies may be silent Fc variants, showing a reduced Fcγ mediated CD40 receptor cross-linking. Respective mutations of the human IgG1 FC region are described in for example US 2018/0118843.

In recently designed immunomodulatory approaches, CD40-targeting agonist monoclonal antibodies (mAbs) are used to enhance the ability of the immune system to recognize and destroy cancer cells. Respective pre-clinical studies have shown that agonistic CD40 mAb can activate APC and promote antitumor T-cell responses and to foster cytotoxic myeloid cells with the potential to control cancer in the absence of T-cell immunity. Thus, agonistic CD40 mAb are fundamentally different from mAb that accomplish immune activation by blocking negative check-point molecules such as CTLA-4 or PD-1.

CP-870,893 is the first fully human IgG2 mAb that operates as a potent and selective agonist of CD40. Interestingly, binding of CP-870,893 does not compete with CD154 binding to CD40. In preclinical studies, CP-870,893 has been shown to mediate both immune system-dependent and -independent effects on tumor cell survival. In the first-in-human study, promising antitumor activity was observed, especially in patients with melanoma. Pharmacodynamically, the administration of CP-870,893 leads to a transient decrease in peripheral blood B cells and to the upregulation of activation markers on APCs.

Thus, agonistic CD40 mAbs represent a promising strategy for novel cancer therapeutics. However, also concerns have been raised in respect to their potential cytotoxic side-effects. Agonistic monoclonal CD40 antibodies stand in prospect of triggering cytokine release syndromes, autoimmune reactions, thromboembolic syndromes (due to the expression of CD40 by platelets and endothelial cells), hyper immune stimulation leading to activation-induced cell death or tolerance, and tumor angiogenesis. These effects may cause untoward toxicity or the promotion of tumor growth. Mechanistically, the ability of agonistic CD40 and other TNF receptor family targeting antibodies to interact with Fcγ receptors has been linked to the occurrence of toxicities in animal studies (Li & Ravetch 2012, Xu et al. 2003, Byrne et al. 2016)

For the strongest agonist tested, CP-870,893, the most common side effect that has been reported is cytokine release syndrome, manifesting as chills, fever, rigors, and other symptoms soon after infusion. Also, several cases of thromboembolic events have been observed with CP-870, 893. With Dacetuzumab, noninfectious inflammatory eye disorders have been observed.

Therefore, there is a need to provide for agonistic CD40 mABs, that exhibit reduced cellular toxicity, leading to fewer clinical side-effects while maintaining their potency and clinical effectiveness. The agonistic CD40 mAbs of the present invention can fulfill this need, allowing for the exploitation of the full immunomodulatory potential of agonistic CD40 antibodies.

SUMMARY ON INVENTION

The present invention provides for monoclonal antibodies or an antigen-binding fragment thereof that specifically bind to human CD40 receptor and induce CD40 signaling independent of Fcγ mediated CD40 receptor crosslinking. More specifically, the antibodies of the present invention bind to a CD40 epitope that overlaps with the epitope of the CD40 ligand and are capable of activating human APCs. The present invention also provides for compositions comprising said antibodies and uses for the antibodies and compositions in the treatment of a condition or disease, in which the stimulation of the immune system is desired, e.g. in the treatment of patients suffering from cancer.

DEFINITIONS

The term "antibody" encompasses the various forms of antibody structures including, but not being limited to, whole antibodies and antibody fragments as long as it shows the properties according to the invention.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multi-specific antibodies formed from antibody fragments.

The terms "monoclonal antibody" or "monoclonal antibody composition" as used herein refer to a preparation of antibody molecules of a single amino acid composition.

The term "humanized antibody" or "humanized version of an antibody" refers to antibodies for which both heavy and light chains are humanized as a result of antibody engineering. A humanized chain is typically a chain in which the V-region amino acid sequence has been changed so that, analyzed as a whole, is closer in homology to a human germline sequence than to the germline sequence of the species of origin. Humanization assessment is based on the resulting amino acid sequence and not on the methodology per se.

The terms "specifically binding, against target, or anti-target antibody", as used herein, refer to binding of the antibody to the respective antigen (target) or antigen-expressing cell, measured by ELISA, wherein said ELISA preferably comprises coating the respective antigen to a solid support, adding said antibody under conditions to allow the formation of an immune complex with the respective antigen or protein, detecting said immune complex by measuring the Optical Density values (OD) using a secondary antibody binding to an antibody according to the invention and using a peroxidase-mediated color development.

The term "antigen" according to the invention refers to the antigen used for immunization or a protein comprising said antigen as part of its protein sequence. For example, for immunization a fragment of the extracellular domain of a protein (e.g. the first 20 amino acids) can be used and for detection/assay and the like the extracellular domain of the protein or the full-length protein can be used.

The term "specifically binding" or "specifically recognized" herein means that an antibody exhibits appreciable affinity for an antigen and, preferably, does not exhibit significant cross-reactivity.

An antibody that "does not exhibit significant cross-reactivity" is one that will not appreciably bind to an undesirable other protein. Specific binding can be determined according to any art-recognized means for determining such binding, e.g. by competitive binding assays such as ELISA.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more.

The "variable region (or domain) of an antibody according to the invention" (variable region of a light chain (VL), variable region of a heavy chain (VH)) as used herein denotes each of the pair of light and heavy chain regions which are involved directly in binding the antibody to the antigen. The variable light and heavy chain regions have the same general structure and each region comprises four framework (FR) regions whose sequences are widely conserved, connected by three complementary determining regions, CDRs.

The term "antigen-binding portion of an antibody" when used herein refers to the amino acid residues of an antibody which are responsible for antigen-binding. The antigen-binding portion of an antibody comprises preferably amino acid residues from the "complementary determining regions" or "CDRs". The CDR sequences are defined according to Kabat et al, Sequences of Proteins of Immunological Interest, 5th Ed. Public Health Service, National Institutes of Health, Bethesda, Md. (1991). Using this numbering system, the actual linear amino acid sequence may contain fewer or additional amino acids corresponding to a shortening of, or insertion into, a FR or CDR of the variable region. For example, a heavy chain variable region may include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The "constant domains (constant parts)" are not involved directly in binding of an antibody to an antigen, but exhibit e.g. also effector functions. The heavy chain constant region gene fragment that corresponds to human IgG1 is called γ1 chain. The heavy chain constant region gene fragment that correspond to human IgG3 is called γ3 chain. Human constant γ heavy chains are described in detail by Kabat, E. A. et al., Sequences of Proteins of Immunological Interest, 5th ed., Public Health Service, National Institutes of Health, Bethesda, Md. (1991), and by Brueggemann, M., et al., J. Exp. Med. 166 (1987) 1351-1361; Love, T. W., et al., Methods Enzymol. 178 (1989) 515-527.

The term "Fc region" herein is used to define a C-terminal region of an immunoglobulin heavy chain that contains at least a portion of the constant region. The term includes native sequence Fc regions and variant Fc regions.

Unless otherwise specified herein, numbering of amino acid residues in the Fc region or constant region is according to the EU numbering system, also called the EU index, as described in Kabat, et al., Sequences of Proteins of Immunological Interest, 5th Ed. Public Health Service, National Institutes of Health, Bethesda, Md. (1991).

A "variant Fc region" comprises an amino acid sequence which differs from that of a "native" or "wildtype" sequence Fc region by virtue of at least one "amino acid modification" as herein defined.

The term "Fc-variant" as used herein refers to a polypeptide comprising a modification in the Fc domain. The modification can be an addition, deletion, or substitution. Substitutions can include naturally occurring amino acids and non-naturally occurring amino acids. Variants may comprise non-natural amino acids.

The term "Fc region-containing polypeptide" refers to a polypeptide, such as an antibody, which comprises an Fc region.

The terms "Fc receptor" or "FcR" are used to describe a receptor that binds to the Fc region of an antibody. A FcR which binds an IgG antibody (a gamma receptor) includes receptors of the FcγRI, FcγRII, and FcγRIII subclasses, including allelic variants and alternatively spliced forms of these receptors. FcγRII FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain, (see review in Daeron, M., Annu. Rev. Immunol. 15 (1997) 203-234). FcRs are reviewed in Ravetch, and Kinet, Annu. Rev. Immunol 9 (1991) 457-492; Capel, et al., Immunomethods 4 (1994) 25-34; and de Haas, et al., J. Lab. Clin. Med. 126 (1995) 330-41. Other FcRs, including those to be identified in the future, are encompassed by the term "FcR" herein. The term also includes the neonatal receptor, FcRn, which is responsible for the transfer of maternal IgGs to the fetus (Guyer, et al., J. Immunol. 117 (1976) 587 and Kim, et al., J. Immunol. 24 (1994) 249).

By "IgG Fc ligand" as used herein is meant a molecule, preferably a polypeptide, from any organism that binds to the Fc region of an IgG antibody to form an Fc/Fc ligand complex. Fc ligands include but are not limited to FcγRs, FcRn, C1q, C3, mannan binding lectin, mannose receptor, staphylococcal protein A, streptococcal protein G, and viral FcγR. Fc ligands also include Fc receptor homologs (FcRH), which are a family of Fc receptors that are homologous to the FcγRs (Davis, et al., Immunological Reviews 190 (2002) 123-136, entirely incorporated by reference). Fc ligands may include undiscovered molecules that bind Fc. Particular IgG Fc ligands are FcRn and Fc gamma receptors. By "Fc ligand" as used herein is meant a molecule, preferably a polypeptide, from any organism that binds to the Fc region of an antibody to form an Fc/Fc ligand complex.

By "Fc gamma receptor", "FcγR" or "FcgammaR" as used herein is meant any member of the family of proteins that bind the IgG antibody Fc region and is encoded by an FcγR gene. In humans this family includes but is not limited to FcγRI (CD64), including isoforms FcγRIA, FcγRIB, and FcγRIC; FcγRII (CD32), including isoforms FcγRIIA (including allotypes H131 and R131), FcγRIIB (including FcγRIIB-1 and FcγRIIB-2), and FcγRIIc; and FcγRIII FcγRIII (CD 16), including isoforms FcγRIIIA (including allotypes V158 and F158) and FcγRIIIb (including allotypes FcγRIIB-NA1 and FcγRIIB-NA2) (Jefferis, et al., Immunol Lett 82(2002)), as well as any undiscovered human FcγRs or FcγR isoforms or allotypes. An FcγR may be from any organism, including but not limited to humans, mice, rats, rabbits, and monkeys. Mouse FcγRs include but are not limited to FcγRI (CD64), FcγRII (CD32), FcγRIII (CD 16), and FCYRIII-2 (CD 16-2), as well as any undiscovered mouse FcγRs or FcγR isoforms or allotypes.

By "FcRn" or "neonatal Fc Receptor" as used herein refers to a protein that binds the IgG antibody Fc region and is encoded at least in part by an FcRn gene. The FcRn may be from any organism, including but not limited to humans, mice, rats, rabbits, and monkeys. As is known in the art, the functional FcRn protein comprises two polypeptides, often referred to as the heavy chain and light chain. The light chain is beta-2-microglobulin and the heavy chain is encoded by the FcRn gene. Unless otherwise noted herein, FcRn or an FcRn protein refers to the complex of FcRn heavy chain with beta-2-microglobulin.

"Percent (%) amino acid sequence identity" with respect to a peptide or polypeptide sequence is defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software.

"Antibody-dependent cell-mediated cytotoxicity" and "ADCC" refer to a cell mediated reaction in which nonspecific cytotoxic cells that express FcRs (e.g. Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch, and Kinet, Annu. Rev. Immunol 9 (1991) 457-492.

The term "Antibody-dependent cellular phagocytosis" and "ADCP" refer to a process by which antibody-coated cells are internalized, either in whole or in part, by phagocytic immune cells (e.g., macrophages, neutrophils and dendritic cells) that bind to an immunoglobulin Fc region.

The term "antibody effector function(s)" or "effector function" as used herein refers to a function contributed by an Fc effector domain(s) of an IgG (e.g., the Fc region of an immunoglobulin). Such function can be effected by, for example, binding of an Fc effector domain(s) to an Fc receptor on an immune cell with phagocytic or lytic activity or by binding of an Fc effector domain(s) to components of the complement system. Typical effector functions are ADCC, ADCP and CDC.

"C1q" is a polypeptide that includes a binding site for the Fc region of an immunoglobulin. C1q together with two serine proteases, C1r and C1s, forms the complex C1, the first component of the complement dependent cytotoxicity (CDC) pathway.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively.

An "effective amount" of an agent, e.g., a pharmaceutical formulation, refers to an amount effective, at dosages and for periods of time necessary, to achieve the desired therapeutic or prophylactic result.

The term "cancer" as used herein may be, for example, lung cancer, non-small cell lung (NSCL) cancer, bronchioloalviolar cell lung cancer, bone cancer, pancreatic cancer, advanced pancreatic carcinoma skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwanomas, ependymonas, medulloblastomas, meningiomas, squamous cell carcinomas, pituitary adenoma, lymphoma, lymphocytic leukemia, including refractory versions of any of the above cancers, or a combination of one or more of the above cancers.

DETAILED DESCRIPTION OF THE INVENTION

The present invention serves the need for providing agonistic CD40 mABs that exhibit a reduced cellular toxicity, leading to fewer clinical side-effects while their signaling potency and clinical effectiveness is at least maintained, if not increased, compared to agonistic CD40 antibodies of prior art.

The antibodies or an antigen-binding fragment of the present invention, provide for these advantageous properties as they are capable of specifically binding to the human CD40 receptor and of inducing CD40 signaling independent of Fcγ mediated CD40 receptor crosslinking.

In preferred embodiments, the antibodies according to the invention are humanized IgG1LALA antibodies, humanized IgG1-type antibodies, having at least two alanine amino acids at positions 234 and 235 of the human Fc1 region. Thus, according to a preferred embodiment, a IgG1LALA comprises the mutation L234A and L235A of the human Fc1 region.

Further preferred is that the antibodies according to invention are recombinant molecules.

It is provided by the present invention that an agonistic monoclonal antibody, or an antigen-binding fragment thereof, is capable of binding to the human CD40 receptor and inducing CD40 signaling independent of Fcγ mediated CD40 receptor crosslinking (see also Example 5, FIG. 6 and text below). Furthermore, an antibody according to the present invention may exhibit reduced or depleted signaling capacity through the human Fcγ receptor when compared to the wildtype IgG Fcγ receptor signaling or to Fcγ signaling of antibodies of prior art.

In certain embodiments, the agonistic monoclonal CD40 antibodies of the invention, or antigen-binding fragments thereof, may exhibit a reduced or depleted affinity to human Fcγ receptors compared to the wildtype IgG Fcγ. According to a preferred embodiment, inventive antibodies do not bind to Fcγ receptors—correspondingly the inventive antibodies do not trigger Fcγ mediated CD40 receptor crosslinking.

In a preferred embodiment, the antibodies of the present invention comprise at least amino acid substitutions at L234A and L235A of the human IgG1 Fc region or S228P and L235E of the human IgG4 Fc region.

Figure 16:
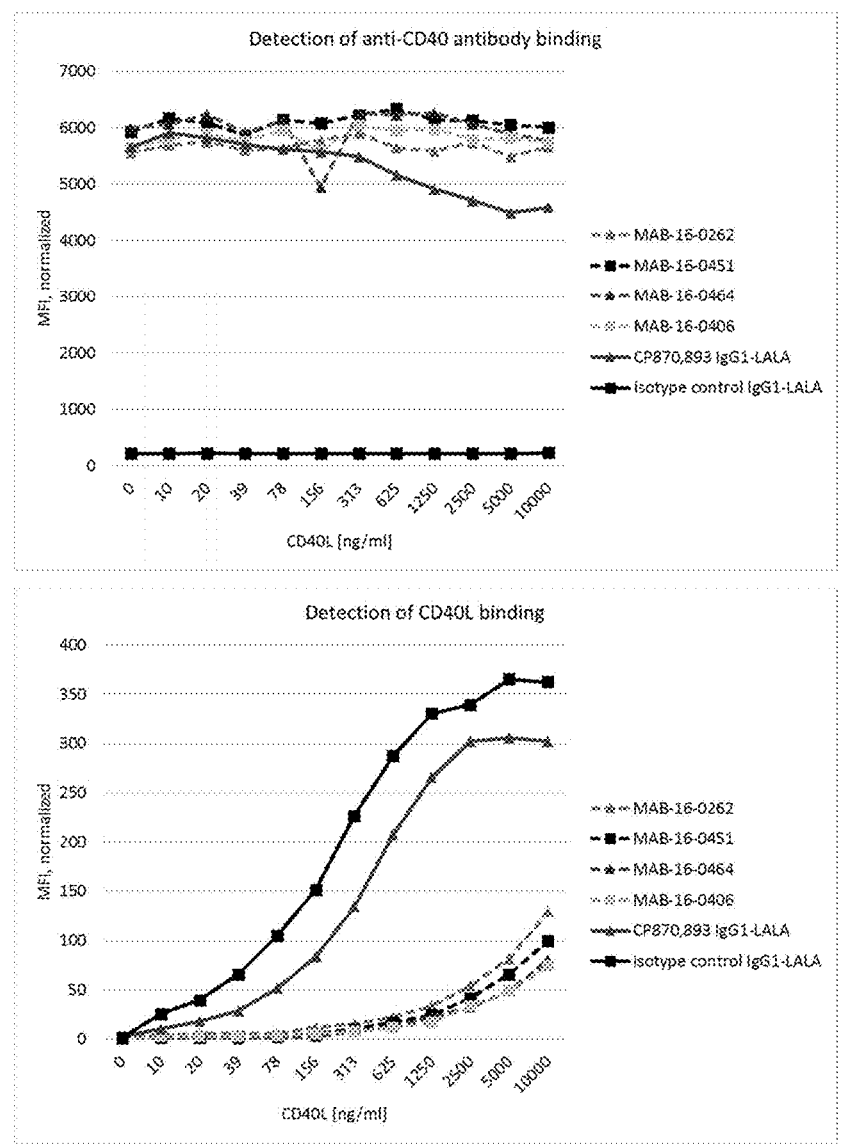
Figure 19:
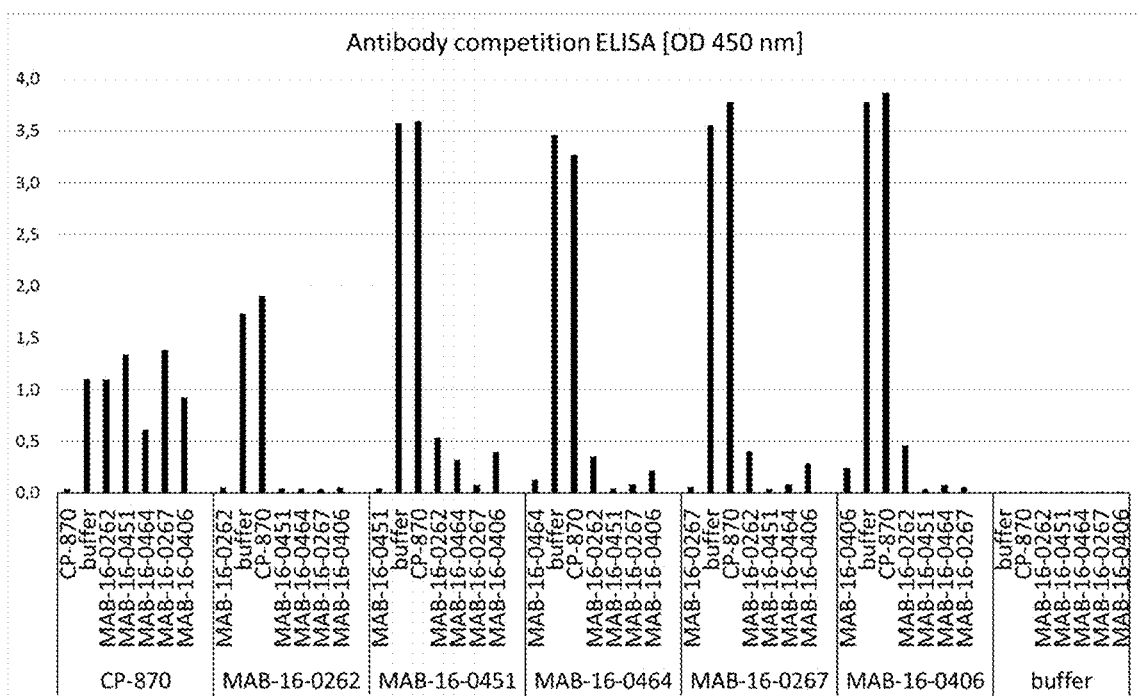

It is further preferred for the present invention that the antibodies bind to a CD40 epitope which overlaps with the CD40L binding site. FIGS. 3 and 16 demonstrate this epitope overlap for the humanized anti-CD40 IgG1-LALA antibodies tested. Also preferred is that the CD40 antibodies compete with CD40L for binding to the CD40 receptor. In epitope competition assays, the antibodies of the invention therefore compete with CD40L. Such assays are described in Examples 3 and 11 and results of experiments with antibodies of the invention are depicted in FIGS. 3 and 16. Thus, according to a further preferred embodiment, the inventive antibodies inhibit CD40L binding to the CD40 receptor. FIG. 19 demonstrates that the antibodies of the invention do not compete with CP-870,893 for binding to CD40.

Antibodies according to the invention possess a very high binding activity to the CD40 receptor. Therefore, in a cell binding assay as outlined in Example 1, the antibodies according to the invention exhibit a binding activity with an EC50 of at most 49.5 ng/ml. Preferably, the EC50 is less than 25 ng/ml, more preferably less than 15 ng/ml, less than 9 ng/ml, 7 ng/ml, 6 ng/ml, 5 ng/ml, 4 ng/ml. Most preferred, the EC50 is 3 ng/ml in a cell binding assay as described in Example 1 and as depicted in FIG. 1.

The humanized agonistic anti-CD40 antibodies according to the invention may be characterized by biochemical affinities for soluble human or cynomolgus monkey CD40 trimeric protein (cf. Example 13; FIG. 18). The inventive antibodies may show KD values of equal or less than 15.7 nM for human CD40. The inventive antibodies may be cross-reactive with cynomolgus monkey CD40 protein with a KD value equal or less than 10.3 nM.

Furthermore, the antibodies of the present invention are capable of inducing cellular NF-κB signaling with high potency. A summary of experiments (cf. Example 2) is depicted in FIG. 2, showing EC50 binding values ranging from 1127 to 6243 ng/ml. The EC50 values demonstrate the great potency of the antibodies to induce NF-kB signaling.

It will also be appreciated that the antibodies of the invention can bind to cynomolgus monkey-CD40. The binding activity of the humanized anti-CD40 IgG1-LALA monoclonal antibodies to cynomolgus monkey (*Macaca fascicularis*) is shown in ELISA experiments using recombinant cynomolgus monkey CD40 recombinant protein (cf. Example 4). The EC50 values shown in FIG. 4 indicate a potent binding of the antibodies.

Another characteristic of the antibodies of the present invention is that they can activate human APCs. For example, the antibodies can activate cells selected from the group comprising dendritic cells (DCs), B-cells, monocytes and myeloid cells. Preferably, the antibodies activate DCs.

This potent CD40 agonistic activity in activating APCs is not due to Fcγ-receptor mediated crosslinking of CD40 proteins (c.f. results of experiments shown in FIGS. 5, 6 and 7 and described in Example 5).

As such, in one embodiment, the antibodies of the present invention induce the release of IL-12p40 in a dendritic cell maturation assay as described in Example 5. The results of experiments conducted with the antibodies of the present invention in such assay are shown in FIGS. 5 to 7.

Figure 13:
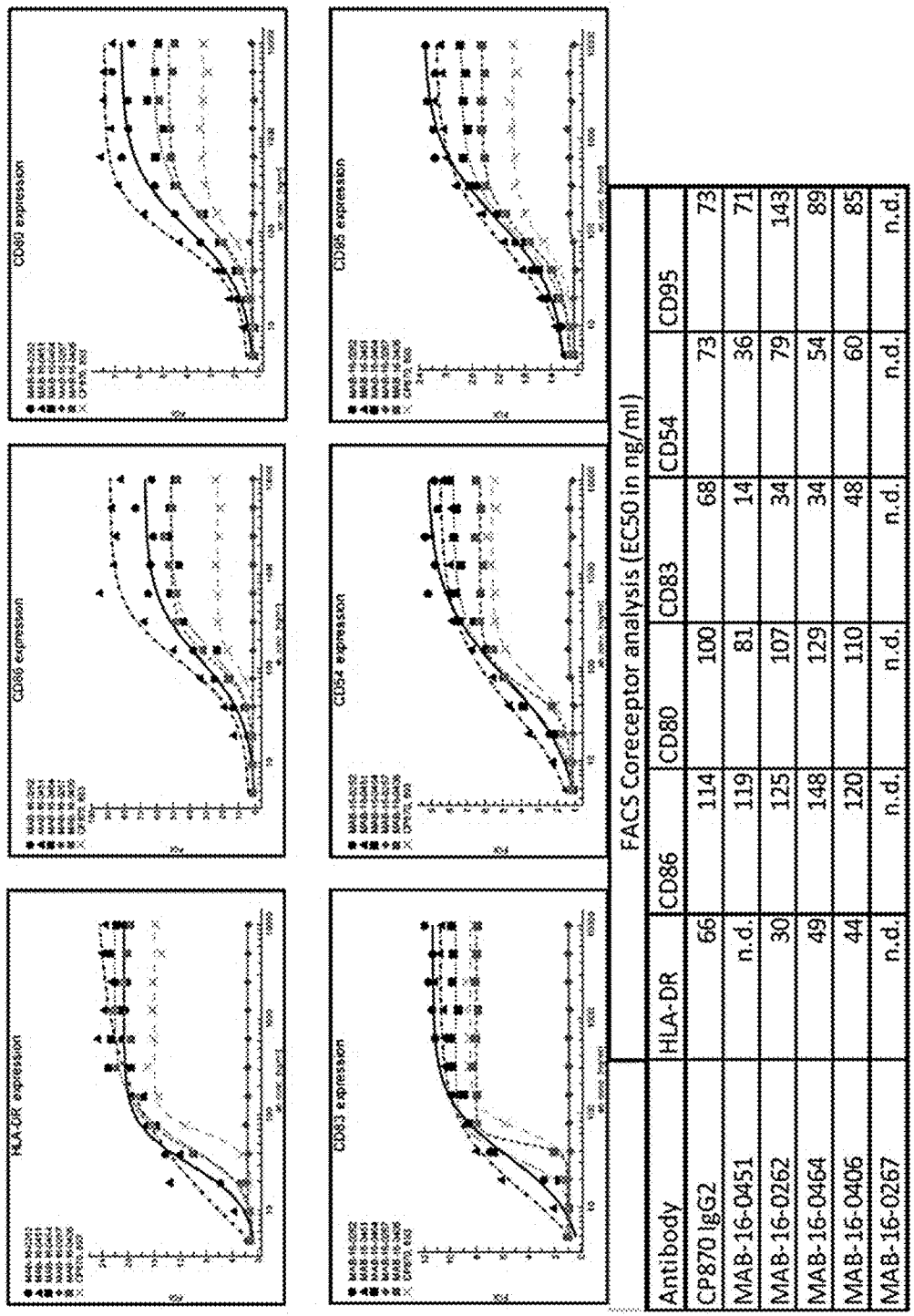
Figure 14:
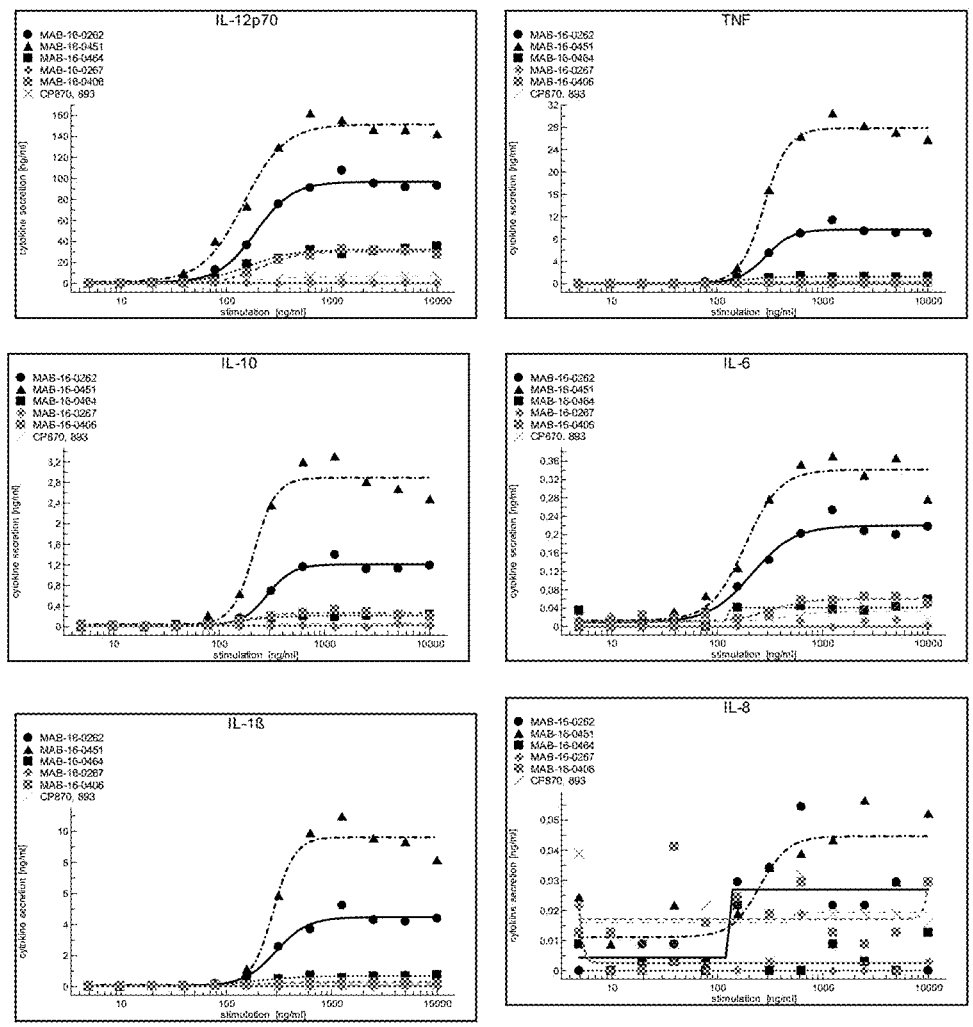

According to a further preferred embodiment, the inventive antibodies induce maturation of antigen-presenting cells as determined by IL12p70 release which is at least equal to the release that is induced upon stimulation with the antibody CP-870,893-IgG2 and with a EC50 value of equal or less than 208 ng/ml (FIGS. 12 and 14). Furthermore, the inventive antibodies induce maturation of antigen-presenting cells as determined by the induction of CD86 by at least 7.5 fold and with an EC50 of equal or less than 148 ng/ml (FIGS. 11 and 13).

Preferably, the antibodies induce a release of IL12p40 from monocyte derived DCs that is at least equal to the release that is induced upon stimulation with the antibody CP-870,893-IgG2 (cf. FIG. 6). As said before, this potential to induce DC maturation is not due to signaling via the Fc receptors. The humanized anti-CD40 IgG1-LALA monoclonal antibodies of the invention potently induce monocyte derived dendritic cell activation in an Fcγ receptor-independent manner (see Example 5 and FIG. 6). FIG. 6 demonstrates that levels of IL12p40 release induced by CP-870,893 variants correlate with the variants ability to bind Fc receptors (IgG1-LALA<IgG2<IgG1<IgG1-V11). Strikingly, stimulation by humanized anti-CD40 IgG1-LALA monoclonal antibodies of the invention resulted in Fc-independent IL12p40 secretion levels which covered and even exceeded the range yielded with the CP-870,893 variants. Thus, the anti-CD40 antibodies of the invention provide potent agonistic activity on primary, monocyte derived dendritic cells without Fcγ-receptor mediated crosslinking of CD40 proteins.

Furthermore, the antibodies of the present invention are very specific in their activation. They do not induce a general release of inflammatory cytokines, such as TNF-alpha (c.f. Example 6 and FIG. 8).

Another characteristic of the antibodies of the present invention is the reduced clearance of antibodies from the cell surface. CP-870,893 is known to internalize after binding to the CD40 receptor on cells. Clinical studies showed that CP-870,893 is cleared from the circulation in patients rapidly with an estimated half-life of less than 6 hours reflecting a large CD40 receptor sink in patients which may be caused by cellular internalization (Rüter et al 2010).

Figure 9:
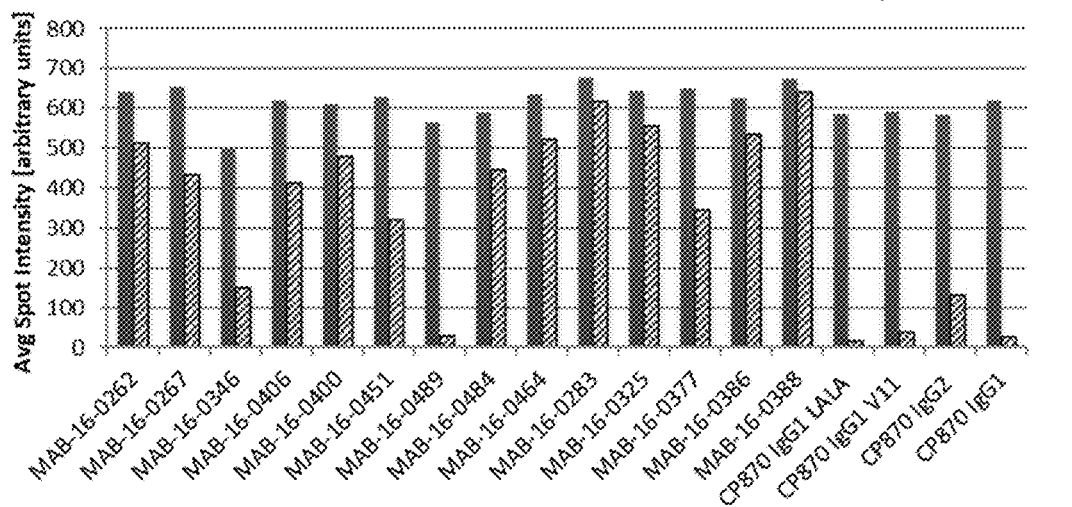

Antibodies of the invention are retained at the cell surface under conditions allowing endocytosis and internalization (c.f. Example 7 and FIG. 9). In contrast, CP-870,893 variants are not retained at the cell surface under conditions allowing endocytosis and internalization (FIG. 9).

It will be appreciated that the antibodies according to the invention have an indirect (immune-mediated) effect on tumor cell death. Thus, the antibodies exhibit an indirect immune cell-mediated cytotoxic effect on tumor cells.

In one specific embodiment, the antibodies according to the invention do not result in depletion of immune cells expressing CD40 by mechanisms of ADCC, ADCP or CDC.

Thus, in summary, the inventive antibodies may be further characterized by
(a) no binding to the Fcγ Receptor;
(b) having a CD40 cell binding affinity with a EC50 value of equal or less than about 49.5 ng/ml;
(c) having KD values of equal or less than about 15.7 nM;
(d) being cross reactive to cynomolgus monkey CD40 with a KD value equal or less than about 10.3 nM;
(e) inhibiting CD40L by binding to CD40;
(f) prevent synergistic and additive effects of CD40L-mediated functions;
(g) inducing maturation of antigen presenting cells as determined by IL12p70 release which is at least equal to the release that is induced upon stimulation with the antibody CP-870,893-IgG2 and with an EC50 value of equal or less than about 208 ng/ml
and/or as determined by the induction of CD86 on dendritic
 cells by at least 7.5-fold and with an EC50 of equal or less than about 148 ng/ml; and/or
(h) reducing the level of CD40 on the cell surface to a lesser extent than CP-870,893.

According to a preferred embodiment, the inventive antibodies are characterized by having at least one, two, three, four, five, six, seven or eight or all of the above properties (a to h).

Due to the favorable properties of the antibodies of the invention, they are capable of inhibiting the growth of human tumors.

In certain embodiments, an antibody according to the invention may comprise a VH region selected from the group of VH regions comprising the CDR regions selected from the group consisting of a CDR1H region of SEQ ID NO: 29+n, a CDR2H region of SEQ ID NO: 43+n and a CDR3H region of SEQ ID NO: 57+n, wherein n is a number selected from the group consisting of 0 to 13, and a VL region selected from the group of VL regions comprising CDR regions selected from the group consisting of a CDR1L region of SEQ ID NO: 71+m, a CDR2L region of SEQ ID NO: 85+m and a CDR3L region of SEQ ID NO: 99+m, wherein m is a number selected from the group consisting of 0 to 13, and wherein the CDRs may comprise any one or more amino acid mutations that does not diminish their activity according to the invention.

Preferably, the antibody comprises a VH region selected from the group of VH regions comprising the CDR regions selected from the group consisting of a CDR1H region of SEQ ID NO: 29+n, a CDR2H region of SEQ ID NO: 43+n and a CDR3H region of SEQ ID NO: 57+n, wherein n is a number selected from the group consisting of 0 to 13, and a VL region selected from the group of VL regions comprising CDR regions selected from the group consisting of a CDR1L region of SEQ ID NO: 71+m, a CDR2L region of SEQ ID NO: 85+m and a CDR3L region of SEQ ID NO: 99+m, wherein m is a number selected from the group consisting of 0 to 13.

In certain embodiments, an antibody according to the invention may comprise a VH region selected from the group of VH regions comprising the CDR regions selected from the group consisting of a CDR1H region of SEQ ID NO: 29+n, a CDR2H region of SEQ ID NO: 43+n and a CDR3H region of SEQ ID NO: 57+n, and a VL region selected from the group of VL regions comprising CDR regions selected from the group consisting of a CDR1L region of SEQ ID NO: 71+n, a CDR2L region of SEQ ID NO: 85+n and a CDR3L region of SEQ ID NO: 99+n, wherein n is a number selected from the group consisting of 0 to 13, and wherein the CDRs may comprise any one or more amino acid mutations that does not diminish their activity according to the invention.

Preferably, the CDRs have a sequence identity to their respective SEQ ID NOs of at least 91%, preferably 92%, 93%, 94%, 95%, 96%, 97%, 98%, or 99%.

In another embodiment, the antibodies or antigen-binding fragments according to invention comprise a heavy chain variable (VH) region that is least 60% identical, preferably at least 70% identical, more preferably at least 80% identical, more preferably at least 85% identical to a VH region selected from the group consisting of VH regions of SEQ ID NO: 1 to 14.

Preferably, said antibodies comprise a heavy chain variable region (VH) sequence having at least 86%, 87%, 88%, 89%, 90%, 91%, 92%, 93%, 94%, 95%, 96%, 97%, 98%, 99%, or 100% sequence identity to an amino acid sequence selected from the group of VH sequences of SEQ ID NO: 1 to 14.

In certain embodiments, a VH sequence having at least 60%, 70%, 80%, 85%, 86%, 87%, 88%, 89%, 90%, 91%, 92%, 93%, 94%, 95%, 96%, 97%, 98%, or 99% identity contains substitutions (e.g., conservative substitutions), insertions, or deletions relative to the reference sequence, whereby the antibody retains the ability to bind specifically according to the invention to the respective antigen.

The present invention also encompasses an antibody that comprises a heavy chain variable region (VH) comprising an amino acid sequence selected from the group of SEQ ID NO: 1 to 14.

Preferably, the heavy chain variable region (VH) sequence is SEQ ID NO:1, alternatively SEQ ID NO:2, or SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, The present invention also relates to an antibody that comprises a light chain variable (VL) region that is least 60% identical, preferably at least 70% identical, more preferably at least 80% identical, more preferably at least 85% identical to a VL region selected from the group consisting of VL regions of SEQ ID NO: 15 to 28.

Preferably, said antibodies comprise a VL sequence having at least 86%, 87%, 88%, 89%, 90%, 91%, 92%, 93%, 94%, 95%, 96%, 97%, 98%, 99%, or 100% sequence identity to an amino acid sequence selected from the group of VL sequences of SEQ ID NO: 15 to 28.

In certain embodiments, a VL sequence having at least 60%, 70%, 80%, 85%, 86%, 87%, 88%, 89%, 90%, 91%, 92%, 93%, 94%, 95%, 96%, 97%, 98%, or 99% identity contains substitutions (e.g., conservative substitutions), insertions, or deletions relative to the reference sequence, whereby the antibody retains the ability to bind specifically according to the invention to the respective antigen.

The present invention also encompasses an antibody that comprises a light chain variable region (VL) comprising an amino acid sequence selected from the group of SEQ ID NO: 15 to 28.

Preferably, the light chain variable region (VL) sequence is SEQ ID NO:15, alternatively SEQ ID NO:16, or SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, or SEQ ID NO:28.

In certain embodiments, a total of 1 to 10 amino acids have been substituted, inserted and/or deleted in said VL sequences. In other embodiments, a total of 1 to 10 amino acids have been substituted, inserted and/or deleted in said VH sequences. In certain embodiments, a total of 1 to 10 amino acids have been substituted, inserted and/or deleted in each of said VH or VL sequences. Said substitutions, insertions, or deletions may occur in regions outside the CDRs (i.e., in the FRs).

The invention also comprises affinity matured antibodies which can be produced according to methods known in the art. Marks et al. Bio/Technology 10:779-783 (1992) describes affinity maturation by VH and VL domain shuffling. Random mutagenesis of CDR and/or framework residues is described by: Barbas et al., Proc Nat. Acad. Sci, USA 91: 3809-3813 (1994); Schier et al., Gene 169: 147-155 (1995); Yelton et al., J. Immunol. 1 55:1994-2004 (1995); Jackson et al., J. Immunol. 1 54(7):3310-9 (1995); and Hawkins et al., J. Mol. Biol. 226:889-896 (1992) and WO2010/108127.

Figure 10:
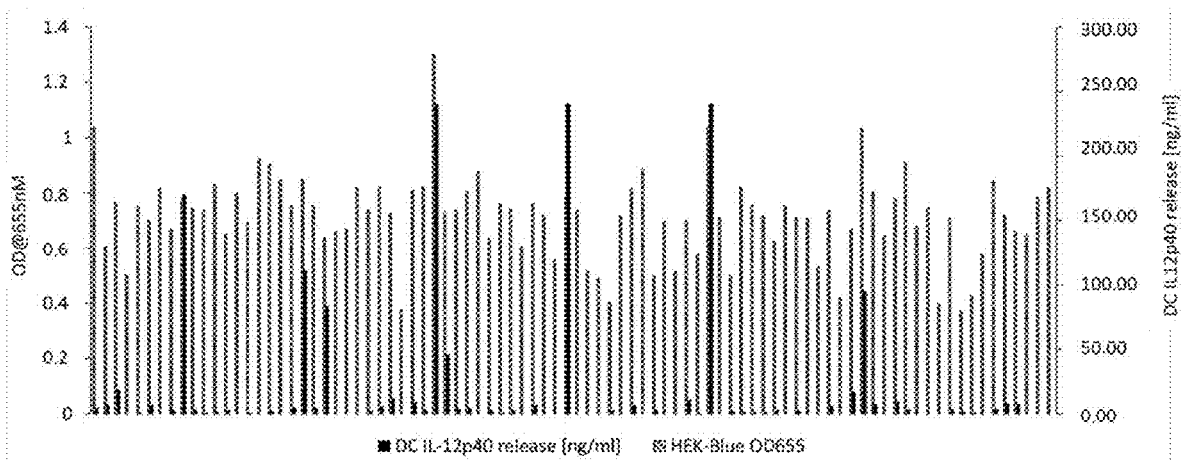

The present invention also encompasses an antibody that comprises a VH region and a VL region comprising the respective CDR1, CDR2 and CDR3 regions of an antibody selected from the group comprising of the antibodies listed in FIG. 10, i.e. comprising the antibodies MAB-16-0283, MAB-16-0377, MAB-16-0267, MAB-16-0386, MAB-16-0451, MAB-16-0346, MAB-16-0325, MAB-16-0388, MAB-16-0464, MAB-16-0262, MAB-16-0406, MAB-16-0484, MAB-16-0400, MAB-16-0489.

The present invention also encompasses an antibody that comprises the SEQ ID NO.: 1 and 15, or SEQ ID NO.: 2 and 16. An antibody according to the invention may also comprise SEQ ID NO.: 3 and 17, or SEQ ID NO.: 4 and 18, or SEQ ID NO.: 5 and 19, or SEQ ID NO.: 6 and 20, or SEQ ID NO.: 7 and 21, or SEQ ID NO.: 8 and 22, or SEQ ID NO.: 9 and 23, or SEQ ID NO.: 10 and 24, or SEQ ID NO.: 11 and 25, or SEQ ID NO.: 12 and 26. Alternatively, an antibody according to the invention comprises SEQ ID NO.: 13 and 27, or SEQ ID NO.: 14 and 28.

In another aspect, the antibodies of the invention are for use in the treatment of patients suffering from cancer.

Said cancer can be one or more of the types of cancer selected from the group comprising pancreas cancer, advanced pancreatic carcinoma lung cancer, non-small cell lung (NSCL) cancer, bronchioloalviolar cell lung cancer, bone cancer, pancreatic cancer, skin cancer, cancer of the head or neck, cutaneous or intraocular melanoma, ovarian cancer, rectal cancer, cancer of the anal region, stomach cancer, gastric cancer, colon cancer, breast cancer, kidney cancer, Hodgkin's lymphoma, liver cancer, Gall bladder cancer, bladder cancer, prostate cancer, thyroid cancer, salivary gland cancer, or uterine cancer.

In certain embodiments, the cancer is a solid tumor.

It is also possible in some embodiments, that the cancer is a CD40 expressing cancer. However, this is not necessary for the effective functioning of the antibodies of the invention.

It will be further appreciated that the antibody of the invention may be used as a sole treatment for cancer in a patient or as part of a combination treatment (which further treatment may be a pharmaceutical cytotoxic or cytostatic agent, radiotherapy, targeted therapy and/or surgery).

Thus, the patient may also receive one or more further treatments for cancer, for example pharmaceutical agents (such as cytotoxic or cytostatic agents, targeted therapy), radiotherapy and/or surgery.

Thus, in some embodiments, the antibody according to the invention is used in the treatment of cancer in combination with cytotoxic or cytostatic agents, radiotherapy, targeted therapy and/or immunotherapy.

The antibodies of the invention can also be used in the treatment of patients that are insufficiently responding and/or resistant to cytotoxic or cytostatic agents, radiotherapy, targeted therapy and/or immune therapy.

Said radiotherapy may be selected from the group comprising external beam radiation therapy, contact x-ray brachytherapy, brachytherapy, systemic radioisotope therapy or intraoperative radiotherapy.

The cytotoxic or cytostatic anti-cancer agents according to the invention may be from the group comprising taxanes, anthracyclins, alkylating agents, histone deacetylase inhibitors, topoisomerase inhibitors, kinase inhibitors, nucleotide analogs, peptide antibiotics, and platinum-based agents.

Preferably the targeted anti-cancer agents are used in targeted therapy and selected from one of the following, or combinations thereof: anti-EGFR compounds such as cetuximab, gefitinib, erlotinib, lapatinib, panitumumab, anti-HER2 compounds such as trastuzumab, ado-trastuzumab emtansine, pertuzumab, VEGF-targeting compounds such as bevacizumab, Aflibercept and Pegaptanib and tyrosine kinase inhibitors such as Sunitinib, Pazopanib, Axitinib, Vandetanib, Cabozantinib and Regorafinib.

In case the patients are receiving immune therapy, this can be immune checkpoint inhibition and one or more immune checkpoint inhibitors may be used. The one or more immune checkpoint inhibitors may be selected from the group comprising anti-PD-L1, anti-PD-1, anti-CTLA-4, anti-CD137, anti-LAG-3, anti-TIM-3, anti-OX40, and/or anti-GITR.

The antibody according to the invention can also be used in combination with an antibody that specifically binds to human PD-L1, CTLA-4, LAG-3, TIM-3, CD137, OX40, GITR and/or in combination with the drug Nivolumab, Pembrolizumab, Urelumab, Utomilumab, Atezolizumab, Avelumab, Durvalumab, Tremelimumab, Ipilimumab.

In some embodiments according to the invention, the antibody is used in the treatment of cancer at a weekly to monthly dosing regimen.

One of the special advantages of this invention is that, due to their mutations in the Fc region, the antibodies exhibit less dose or treatment limiting toxicities, compared to the antibodies of prior art. The antibodies provoke the typical side effects of CD40 antibodies, if at all, only to a very limited extend. Such side effects are conditions selected from the group comprising cytokine release syndrome, thrombosis, cerebral embolism, transaminase elevations, lymphopenia, fatigue, peripheral neuropathy, alopecia, constipation, nausea and neutropenia.

In another aspect, the present invention relates to a pharmaceutical composition comprising a pharmaceutically acceptable carrier and a therapeutically effective amount of the antibody according to the invention.

The pharmaceutical composition according to the invention may be used in the treatment of patients suffering from cancer. Such cancer can be a solid tumor. The cancer can also be selected from the group comprising pancreas cancer, advanced pancreatic carcinoma lung cancer, non-small cell lung (NSCL) cancer, bronchioloalviolar cell lung cancer, bone cancer, pancreatic cancer, skin cancer, cancer of the head or neck, cutaneous or intraocular melanoma, ovarian cancer, rectal cancer, cancer of the anal region, stomach cancer, gastric cancer, colon cancer, breast cancer, kidney cancer, Hodgkin's lymphoma, liver cancer, Gall bladder cancer, bladder cancer, prostate cancer, Thyroid cancer, salivary gland cancer, or uterine cancer.

The composition can also be used in the treatment of cancer in combination with chemotherapy, radiotherapy, targeted therapy and/or immunotherapy. Said immunotherapy can be immune checkpoint inhibition.

The patients treated with said composition may be insufficiently responding and/or resistant to chemotherapy, radiotherapy, targeted therapy and/or immune therapy.

The pharmaceutical composition according to the invention may also be used in the treatment of cancer in combination with one or more cytotoxic, cytostatic or targeted anti-cancer compounds.

It can be used in the treatment of cancer in combination with one or more immune checkpoint inhibitors, wherein said immune checkpoint inhibitors may be selected from the group comprising anti-PD-L1, anti-PD-1, anti-CTLA-4, anti-CD137, anti-LAG-3, anti-TIM-3, anti-OX40, and/or anti-GITR.

The composition can also be used in combination with an antibody that specifically binds to human PD-L1, CTLA-4, LAG-3, TIM-3, CD137, OX40, GITR and/or in combination with the drug Nivolumab, Pembrolizumab, Urelumab, Utomilumab, Atezolizumab, Avelumab, Durvalumab, Tremelimumab, Ipilimumab.

It can also be used in the treatment of cancer at a weekly to monthly dosing regimen.

It will be particularly appreciated by the patients that the antibody and composition according to the invention exhibit any dose or treatment limiting toxicities, if at all, only to a very limited extend, and importantly, to less extend than antibodies and compositions of prior art.

In another aspect, the present invention also relates to methods of treatment, comprising the administration of an effective amount of the antibody according to the invention to individuals in need of. Such individuals may be patients suffering from cancer. Thus, the present invention also relates to methods of treatment of cancer, wherein the cancer may be a solid tumor.

The step of administering to an individual in need thereof may comprise the local administration, for example local administration to a tumor in a patient (for example, intratumourally or peri-tumourally).

As the antibody-based agents of the invention are suitable for use in the treatment of any type of cancer for which CD40 activation may provide a therapeutic benefit, the methods comprising the administration of said antibodies are also suitable for treatment of any type of cancer for which CD40 activation may provide a therapeutic benefit.

For example, the cancer may be selected from the group consisting of: prostate cancer; breast cancer; colorectal cancer; pancreatic cancer; ovarian cancer; lung cancer; cervical cancer; rhabdomyosarcoma; neuroblastoma; multiple myeloma; leukemia, acute lymphoblastic leukemia, melanoma, bladder cancer and glioblastoma.

It will be further appreciated that the methods of treatment according to the invention may comprise the sole administration of the antibody-based agents of the invention to a patient or as part of a combination treatment (which further treatment may be a pharmaceutical cytotoxic or cytostatic agent, radiotherapy, targeted therapy and/or surgery.

In fact, all features and favorable properties of the antibodies of the invention as detailed above, are also reflected and comprised in the methods of treatment and uses of the antibodies according to the invention.

EXAMPLES

The following examples are used in conjunction with the figures and tables to illustrate the invention.

Example 1: Cell Binding of Anti-CD40 Antibodies

To determine the potency of humanized anti-CD40 IgG1-LALA monoclonal antibodies in binding to cell-expressed CD40, HEK-Blue-CD40L™ (InvivoGen) cells were seeded in 25 µl DMEM containing 10% FBS at a cell density of 1000 cells/well in a cell-culture treated, clear bottom 384-well plate. Antibodies were added to final concentrations ranging from L25 µg/ml to 0.01 ng/ml in 5 µl medium. After 24 h cells were washed three times with 25 µl wash buffer (PBS, 0.05% Tween) before Alexa-Fluor-488-conjugated goat anti-human-IgG (Jackson Laboratories) was added at a concentration of 0.8 µg/ml in 20 µl medium. Four hours later, 5 µl Hoechst dye in medium was added to a final concentration of 5 µg/ml. Fluorescent cell binding signals were measured using a CellInsight automated high content imager (Thermo Fisher Scientific). Fitting curves and EC50 calculation were obtained by using Excel (Microsoft) and XLfit (IDBS). FIG. 1 summarizes the EC50 binding values ranging from 3 to 49.5 ng/ml.

Example 2: Induction of Cellular NF-κB Signaling by Anti-CD40 Agonistic Antibodies The agonistic activity of humanized anti-CD40 IgG1-LALA monoclonal antibodies was tested by stimulating HEK-Blue-CD40L™ (InvivoGen) cells which harbor an NF-κB inducible Secreted Embryonic Alkaline Phosphatase (SEAP) gene construct. 25000 cells/well in 20 µl DMEM containing 10% FBS were seeded in a cell-culture treated, clear bottom 384-well plate and cultured overnight. Antibodies were then added in a volume of 5 µl medium to final concentrations ranging from 20 to 0.013 µg/ml. After 6 hours of incubation at 37° C. and 5% CO$_2$, 5 µl of medium supernatant of each well were transferred to a white, clear bottom 384-well plate containing 20 μl of 2×QUANTI-Blue™ reagent (InvivoGen). After incubation for one hour at 37° C. and 5% $CO_2$, optical density at a wavelength of 620 was measured reflecting NF-κB dependent activation of phosphatase secretion. Fitting curves and EC50 calculation were obtained by using Excel (Microsoft) and XLfit (IDBS). EC50 values in FIG. 2 indicate the potency of anti-CD40 antibodies to induce NF-kB signaling in the HEK-Blue-CD40L™ cell line.

Example 3: Competition with CD40L Binding

Competition of humanized anti-CD40 IgG1-LALA monoclonal antibodies with CD40L binding to CD40 was tested using an ELISA assay. CD40L was coated to the surface of a 384-well Nunc™ MaxiSorp™ plate in a volume of 25 μl PBS and at a concentration of 1 μg/ml for one hour at room temperature. Antibodies were pre-incubated at a concentration of 5 μg/ml with recombinant CD40 protein at a concentration of 1.7 μg/ml in a total volume of 40 μl for 1.5 hours at room temperature in ELISA buffer (PBS, 0.5% BSA, 0.05% Tween). The Nunc™ MaxiSorp™ plate was washed three times with wash buffer (PBS, 0.1% Tween) and blocked for one hour at room temperature with PBS, 2% BSA, 0.05% Tween. After three washes in wash buffer, 25 μl of the antibody-CD40 complex were added to the Nunc™ MaxiSorp™ plate wells and incubated for one hour at room temperature. After 3 washes in wash buffer, wells were incubated with 25 μl of a 1:2000 dilution of anti-human peroxidase-linked, species specific F(ab)2 Fragment from goat (AbD Serotec) in ELISA buffer for one hour at room temperature. Wells were washed six times with wash buffer and 30 μl/well TMB substrate solution (Invitrogen) were added. After 10 minutes at room temperature, 30 μl Stop solution (1M HCl) was added per well and absorbance at 450 and 620 nm wavelength was measured using a Tecan M1000 microplate reader. ELISA signal for samples incubated with CP-870,893 indicate the lack of competition with CD40L, while the humanized anti-CD40 IgG1-LALA monoclonal antibodies according to the invention compete with CD40L binding to CD40 (see FIG. 3).

Example 4: Cynomolgus Monkey-CD40 Binding Activity

Binding of humanized anti-CD40 IgG1-LALA monoclonal antibodies to cynomolgus monkey-CD40 protein was tested in a biochemical ELISA. Recombinant cyno-CD40 protein (Acro Biosystems) was incubated in a 384-well Nunc™ MaxiSorp™ plate at a concentration of 0.5 μg/ml in PBS for one hour at room temperature. After washing three times with wash buffer (PBS, 0.1% Tween), plates were blocked with PBS, 2% BSA, 0.05% Tween for one hour at room temperature. Plates were washed again three time with wash buffer and antibodies at concentrations ranging from 500 to 0.03 ng/ml in PBS, 0.5% BSA, 0.05% Tween were incubated for one hour at room temperature. After 3 washes in wash buffer, wells were incubated with 12.5 μl of a 1:3000 dilution of anti-human peroxidase-linked, species specific $F(ab)_2$ Fragment from goat (AbD Serotec) in ELISA buffer for one hour at room temperature. Wells were washed six times with wash buffer and 15 μl/well TMB substrate solution (Invitrogen) were added. After 10 minutes at room temperature 15 μl Stop solution (1M HCl) were added per well and absorbance at 450 and 620 nm wavelength was measured using a Tecan M1000 microplate reader. Fitting curves and EC50 calculation were obtained by using Excel (Microsoft) and XLfit (IDBS). As shown in FIG. 4, most antibodies bind to cyno-CD40 with EC50 values between 8 and 31.8 ng/ml.

Example 5: Induction of Dendritic Cell Maturation a. Monocyte derived dendritic cells were generated to test the ability of humanized anti-CD40 IgG1-LALA monoclonal antibodies to stimulate maturation of dendritic cells as measured by secretion of the IL12p40 cytokine. Human buffy coat preparations from different donors were used to differentiate dendritic cells from monocytes in vitro. Buffy coat received from the Bavarian Red Cross was diluted 1:4 with DPBS and layered on Ficoll-Paque (GE Healthcare) density gradients. After centrifugation, interphase Peripheral Blood Mononuclear Cells (PBMCs) were washed three times with DPBS and monocytes were isolated using magnetic CD14 MicroBeads (Miltenyi Biotec) according to manufacturer's instructions. Monocytes were cultured in RPMI-1640 containing 10% FCS, 1×Pen/Strep, 1× L-Glutamin, 50 ng/ml recombinant human GM-CSF (R&D Systems) and 10 ng/ml recombinant human IL-4 (R&D Systems) at a cell density of $1.2×10^6$ cells/ml in T-175 cell culture flasks. Every 48 hours, 90% of the medium was replaced with fresh, cytokine containing medium. At day five, in vitro differentiated, immature dendritic cells (iDCs) were harvested and distributed to a cell culture 96-well plate at a cell density of $10^6$ cells/ml in 100 μl of the same medium.

b. In one experiment iDCs were stimulated by the addition of anti-CD40 antibodies at a concentration of 5 μg/ml. 48 h after stimulation, secreted IL12p40 cytokine was quantified in the medium supernatant using a commercially available ELISA kit (R&D Systems) according to the manufacturer's instructions. FIG. 5 shows that humanized anti-CD40 IgG1-LALA monoclonal antibodies stimulated IL12p40 release by monocyte derived dendritic cells to different extents, ranging from less that 1 ng/ml to more than 24 ng/ml, whereas a non-CD40 binding control IgG1-LALA antibody did not lead to stimulation of detectable levels of IL12p40.

c. The humanized anti-CD40 IgG1-LALA monoclonal antibodies of the invention are not able to bind to Fcγ receptors which are expressed on monocyte derived dendritic cells. In order to compare these antibodies with antibodies harboring different Fcγ receptor binding activities, we constructed reference CP-870,893 anti-CD40 antibodies containing human IgG1, IgG1-LALA, IgG2 and IgG1-V11 Fc parts and stimulated monocyte derived dendritic cells with different concentrations of these antibodies. The IgG1-V11 form harbors four mutations (G237D, H268D, P271G, A330R) in the heavy chain Fc part. These mutations have been described to selectively increase the affinity to the Fcγ-receptor RIIB (Mimoto et al. 2013). FIG. 6 demonstrates that CP-870,893 variants stimulate IL12p40 release in an Fc-dependent manner (IgG1-LALA<IgG2<IgG1<IgG1-V11). Strikingly, stimulation by humanized anti-CD40 IgG1-LALA monoclonal antibodies of the invention resulted in Fc-independent IL12p40 secretion levels which covered and even exceeded the range yielded with the CP-870,893 variants. The anti-CD40 antibodies of the invention thereby provide potent agonistic activity on primary, monocyte derived dendritic cells without Fcγ-receptor mediated crosslinking of CD40 proteins.

d. In another experiment, the potency of humanized anti-CD40 IgG1-LALA monoclonal antibodies to induce IL12p40 secretion by monocyte derived dendritic cells was determined by stimulation with antibody concentrations ranging from 0.005 to 10 µg/ml. FIG. 7 shows that EC50 values for different antibodies ranged between 380 to 743 ng/ml.

Example 6: TNF-Alpha Release in a High Density PBMC Assay

To determine whether humanized anti-CD40 IgG1-LALA monoclonal antibodies induce general release of cytokines in blood cells, PBMCs were stimulated with the antibodies according to the protocol of Romer et al. 2011. PBMCs were isolated as described before and cultured in RPMI-1640 containing 10% human AB serum and 1× non-essential amino acids (NEAA) at a cell density of $1 \times 10^7$ cells/ml in a T175 cell culture flask. After two days, cells were harvested and seeded at a density of $1 \times 10^6$ cells/ml in triplicates in a 96-well cell culture plate. Antibodies were added at a concentration of 10 µg/ml and incubated with PBMCs for three days at 37° C., 5% $CO_2$ and 95% humidity. As a positive control, an OKT-3 antibody (Abcam) was included in the experiments. TNF-alpha release was quantified in the cell culture supernatant using a commercially available human-TNF-alpha ELISA kit (R&D Systems) according to the manufacturer's instructions. FIG. 8 shows that the anti-CD40 antibodies of the invention and a non-CD40 binding IgG1-LALA control antibody did not stimulate significant release of TNF-alpha by PBMCs, in contrast to the OKT-3 antibody.

Example 7: Cellular Pulse-Chase Assay

Cell binding and internalization dynamics of anti-CD40 antibodies were analyzed in a pulse-chase assay using HEK-Blue-CD40L™ cells (InvivoGen). 2000 Cells/well were seeded in two black 384-well plate with clear bottom in DMEM medium containing 10% FCS. After overnight culture, the anti-CD40 antibodies of the invention and CP-870,893 Fc-variant antibodies as described above were added to one plate at a concentration of 0.8 µg/ml and incubated for 15 min at 37° C. and 5% CO2. Subsequently, both plates were washed three times with cell wash buffer (PBS 0.05% Tween) and incubated for one hour in culture medium. For the last 15 minutes, antibodies were added to plate 2 at a concentration of 0.8 µg/ml. Both plates were then washed three times with cell wash buffer, placed on ice and incubated with 0.8 µg/ml secondary anti-human Alexa-Fluor-488 coupled antibody (Jackson Laboratories) and 5 µg/ml Hoechst stain (Invitrogen) for 30 minutes on ice. Cell surface fluorescent signals were quantified using a CellInsight high content imager (Thermo Fisher Scientific). FIG. 9 shows that CP-870,893 variant antibodies have strongly reduced cell surface signals after one-hour incubation in conditions allowing internalization. In contrast, incubation of many of the anti-CD40 antibodies according to the invention under the same conditions result in only minor reduction of cell surface signals indicating limited internalization rates.

Example 8: Correlation of Gene Reporter Induction and Dendritic Cell Maturation Activity of Humanized Anti-CD40 Antibodies a. Cellular gene reporter (HEK-Blue-CD40L™) and dendritic cell (DC) maturation assays were done as described in examples 2 and 5, respectively. Antibodies were used at 5 µg/ml for the DC assay and at concentrations ranging from 13 to 20000 ng/ml in the HEK-Blue-CD40L™ gene reporter assay. FIG. 10 compares the maximum induction observed in the gene reporter assay with the IL12p40 cytokine release by DCs after stimulation with 5 µg/ml of the antibodies. While all 88 humanized anti-CD40-IgG1-LALA antibodies induce gene reporter expression to similar extents, some antibodies show very high stimulation of IL12p40 release by DCs. HEK-Blue-CD40L™ cells do not express Fcγ receptors. The assay is capturing basic, agonistic activities of CD40 antibodies independent of Fcγ receptor binding. DCs express Fcγ receptors and agonistic activities of anti-CD40 antibodies such as CP-870,893 are dependent on Fcγ receptor binding (Example 5). Nevertheless, while most of the 88 IgG1-LALA antibodies lack strong activation of DCs, a minor fraction can induce very strong activation of DCs without Fcγ receptor mediated crosslinking. Therefore, a highly agonistic anti-CD40 antibody, whose activity on primary dendritic cells is independent of Fcγ-receptor crosslinking, is a rare case and the identification requires to screen a great number of candidate antibodies with basic agonistic activities.

Example 9: Stimulation of Costimulatory Receptors and Cytokine Release on Dendritic Cells by Agonistic Anti-CD40 Antibodies a. To test the activity of humanized, agonistic anti-CD40 IgG1-LALA antibodies in stimulating costimulatory receptor expression and inflammatory cytokine release by DCs, immature, monocyte derived DCs (iDCs) were generated from three independent donors as described in Examples 5. iDCs were treated with the antibodies at a concentration of 2 µg/ml or CD40L (R&D Systems 6245-CL-050) at 20 µg/ml for 48 h. Stimulated, mature DCs were harvested, stained using fluorophore-labelled antibodies against HLA-DR, CD86, CD80, CD83, CD54 and CD95 (all from Miltenyi Biotech) and analyzed by flow cytometry on a BD FACSVerse device. FIG. 11 displays the stimulation of receptor expression as fold of induction over isotype antibody control treatment. The data demonstrates strong induction of costimulatory receptors, in particular CD86. CP-870,893 shows overall lower activity compared to antibodies MAB-16-0262, MAB-16-0451, MAB-16-0464 and MAB-16-0406 of the invention. A further reduction of activity is observed when a CP-870,893 variant containing an IgG1-LALA constant part is used, confirming the Fcγ receptor binding dependency of this antibody.

b. FIG. 12 shows the results of cytokine measurements in the supernatants of DC cultures using a BD human inflammatory cytometric bead array kit (BD #551811) according to manufacturer's instructions. Antibodies MAB-16-0262, MAB-16-0451, MAB-16-0464 and MAB-16-0406 of the invention show very high levels of IL-12-p40 and IL-12p70 release, while other cytokines, e.g. TNF-α, IL-1β, IL-10 and IL-6 are produced and secreted to a far lesser extent. IL-12p40 and IL12p70 release of DCs treated with CP-870,893 IgG2 and IgG1 variants is significantly lower as compared to the release observed with the antibodies of the invention. In similar experiments in vitro differentiated iDCs from three independent donors were treated with agonistic anti-CD40 antibodies for 48 hours at concentrations ranging from 10000 to 5 ng/ml. Receptor expression and cytokine release was analysed as described above. Fitting curves and EC50 calculation were obtained by using Excel (Microsoft) and XLfit (IDBS). Data presented in FIGS. 13 and 14 exemplify dose dependent effects observed in one donor. Results from two further donors showed qualitatively similar effects. In summary, the potency of humanized anti-CD40 antibodies of the invention as determined by EC50 values is similar to that of CP-870,893, while the maximal induced effect, in particular on IL-12 cytokine release and coreceptor expression is significantly greater than that of CP-870,893.

Figure 15:
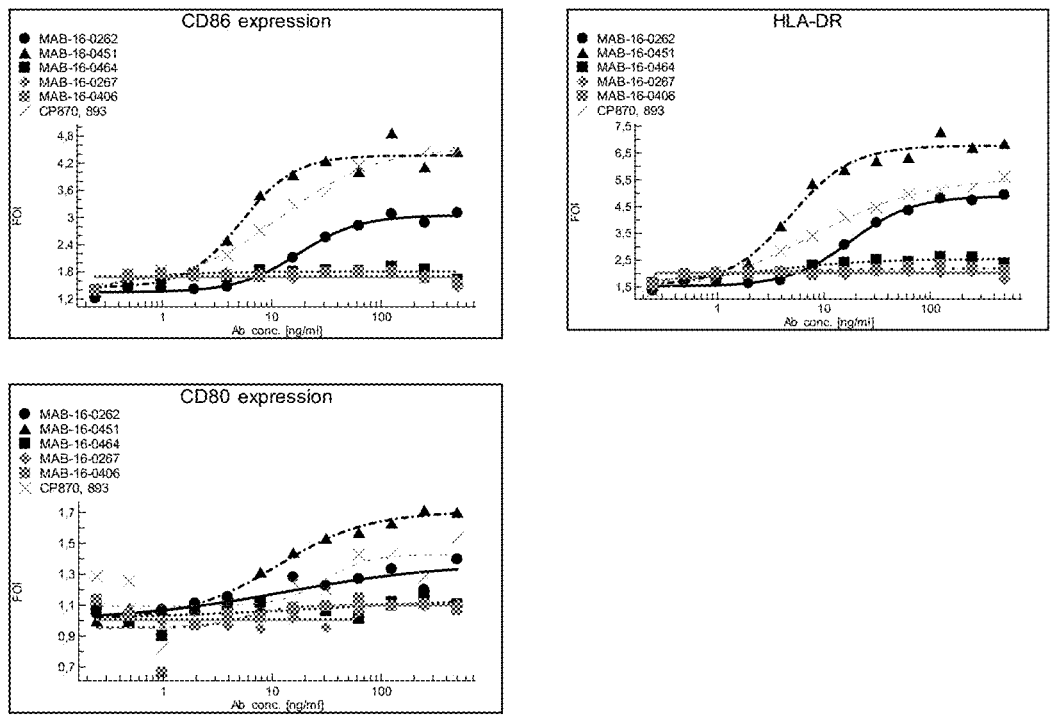

Example 10: Stimulation of Costimulatory Receptors on B-Cells by Agonistic Anti-CD40 Antibodies a. The stimulation of costimulatory receptors by humanized anti-CD40 IgG1-LALA antibodies was also tested on B-cells. PBMCs from three different donors were isolated from human buffy coat by Ficoll density gradient centrifugation and untouched B-cells were purified by negative magnetic enrichment using a B-cell isolation kit II (Miltenyi Biotech) according to manufacturer's instructions. $2 \times 10^5$ B-cells in 100 µl RPMI-1640+10% Human AB Serum were stimulated with antibodies concentration ranging from 500 to 0.2 ng/ml for 48 h. Stimulated B-cells were harvested, stained using fluorophore-labelled antibodies against HLA-DR, CD86 and CD80 (all from Miltenyi Biotech) and analyzed by flow cytometry on a BD FACSVerse device. FIG. 15 displays the dose dependent stimulation of receptor expression in B-cells of one donor as fold of induction over isotype antibody control treatment. Fitting curves and EC50 calculation were obtained by using Excel (Microsoft) and XLfit (IDBS). The results demonstrate that the antibodies of the invention also stimulate costimulatory receptors on B-cells, however, the level of upregulation is lower than that observed in DCs.

Example 11: Competition of CD40L with Anti-CD40 Antibody Binding to CD40 on Cells a. Binding of anti CD40 antibodies of the invention to HEK-Blue-CD40L™ cells in the presence of CD40L was tested to verify whether the antibodies bind to the CD40L binding site of cell surface CD40. HEK-Blue-CD40L™ cells were preincubated with antibodies at their EC90 binding concentration for 30 minutes at 40° C. CD40L containing a mouse-lgG2a Fc-tag (AB Biosciences) was added at concentration ranging from 10000 to 9.8 ng/ml and cells were incubated for 60 minutes at 4° C. Anti-CD40 antibodies and CD40L bound to cell-expressed CD40 were detected using secondary DyLight 405-conjugated anti-mouse lgG and Alexa Fluor 488-conjugated anti-human lgG (Jackson Laboratories) and analyzed using FACSVerse instrument (BD). FIG. 16A shows stable binding of anti-CD40 concentrations except for CP-870,893 whose antibody binding signal slightly decreases at higher CD40L concentrations. CD40L binds to the cells in a dose dependent manner and CP-870,893 does not significantly interfere with CD40L binding (FIG. 16B). In contrast, the antibodies of the invention strongly prevent binding of CD40L to cell-expressed CD40, indicating that these antibodies bind to the CD40L binding site of CD40 and block CD40L from binding CD40 (FIG. 16B).

Figure 17:
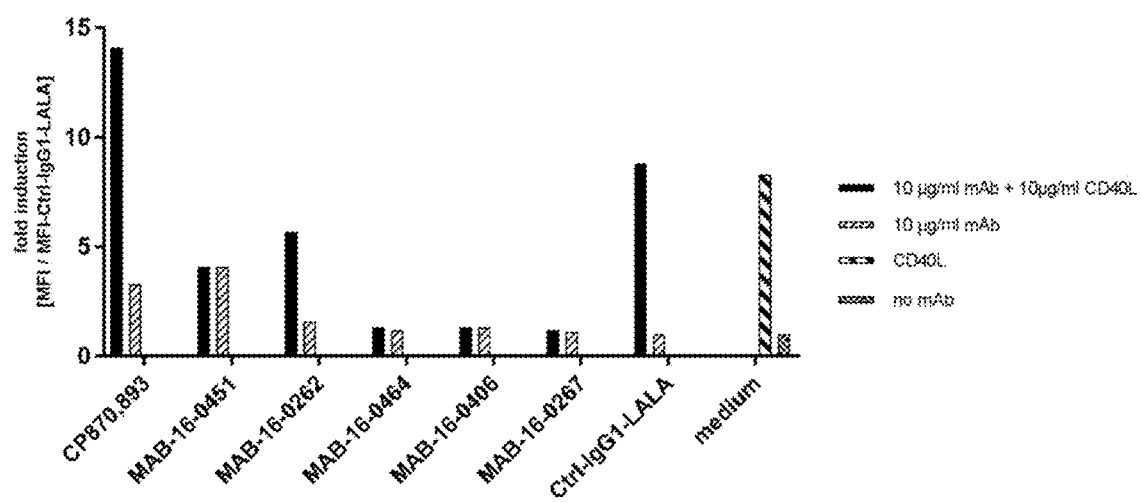

Example 12: Induction of FasR (CD95) Death Receptor Expression by Agonistic CD40 Antibodies in Combination with CD40L a. To test the interference of CD40L with anti-CD40 antibody mediated effects on cells, Ramos cells were treated with CD40L alone or in combination with agonistic anti-CD40 antibodies. Ramos cells were seeded in 96-well plates in RPMI containing 10% FCS at a cell density of $1.25 \times 10^6$ cells/ml. Antibodies were added to the wells at a concentration of 10 µg/ml and the plate was incubated for 10 minutes at 37° C., 5% CO2, 95% humidity. CD40L (R&D Systems) was then added to some wells to a final concentration of 10 µg/ml and the plate was incubated over night at 37° C., 5% CO2, 95% humidity. Cells were washed with DPBS and stained with a FITC-labelled antibody against CD95 (Miltenyi Biotech). FIG. 17 shows that CD95 induction by CP-870,893 is strongly increased by the addition of CD40L, while co-treatment of all tested anti-CD40 antibodies of the invention reduce the effect of CD40L. The data indicates, that agonistic anti-CD40 antibodies of the invention which bind the CD40L binding on CD40, prevent synergistic and additive effects by CD40L and therefore allow controlled and safe pharmacology.

Example 13: Affinities of Humanized, Agonistic Anti-CD40 IgG1-LALA Antibodies a. The biochemical affinities of the antibodies of the invention was determined by surface plasmon resonance measurements. Antibodies were reversibly immobilized to a CM5 sensor chip surface via an anti-human Fc antibody. The kinetics of the interaction of immobilized antibodies with soluble human or cynomolgus monkey CD40 monomeric protein (Acro Biosystems) were analysed on a Biacore T200 SPR instrument. Kinetic data were determined using a Langmuir 1:1 binding model. FIG. 18 demonstrates that antibodies MAB-16-0451 and MAB-16-0464 have a KD of 1.2 and 2.6, whereas MAB-16-0262 and CP-870,893 show $K_D$ values of 15.7 or 8.9, respectively. $K_D$ values generated using cynomolgus monkey CD40 protein demonstrate similar affinities.

Example 14: Competitive Binding of Anti-CD40 Antibodies to CD40 a. To test whether the humanized, agonistic anti-CD40 antibodies of the invention bind to overlapping regions on the CD40 molecule, a competitive binding ELISA was performed. Antibodies were coated to 384-well Maxisorp plates at a concentration of 625 ng/ml in PBS for 60 minutes followed by a blocking step with PBS, 2% BSA, 0.05% Tween for 70 minutes. All antibodies were incubated separately at a concentration of 10 µg/ml in tubes together with 330 ng/ml HIS-tagged CD40 recombinant protein (Acro Biosystems) and 4 µg/ml peroxidase-coupled anti-HIS detection antibody (Sigma-Aldrich) for 60 minutes in ELISA buffer (PBS, 0.5% BSA, 0.05% Tween). The plate was washed three times with PBS, 0.1% Tween before the antibody/HIS-CD40/anti-HIS-peroxidase mixes were added to the wells of the plate. The plate was incubated for 60 minutes. Wells were washed six times with PBS, 0.1% Tween and 15 µl/well TMB substrate solution (Invitrogen) were added. The reaction was stopped with 15 µl/well Stop solution (1M HCl) and absorbance at 450 and 620 nm wavelength was measured using a Tecan M1000 microplate reader. FIG. 19 demonstrates that the antibodies of the invention do not compete with CP-870,893 for binding to CD40. Each antibody, however, competes with any other antibody of the invention, which demonstrates that these antibodies bind to the same region on CD40. Importantly, since the agonistic activities of the antibodies of the invention cover a broad range (Examples 9 and 10), this shows that the paratopes of the agonistic anti-CD40 antibodies primarily determine the agonistic activity of anti-CD40 antibodies.

Figure 20:
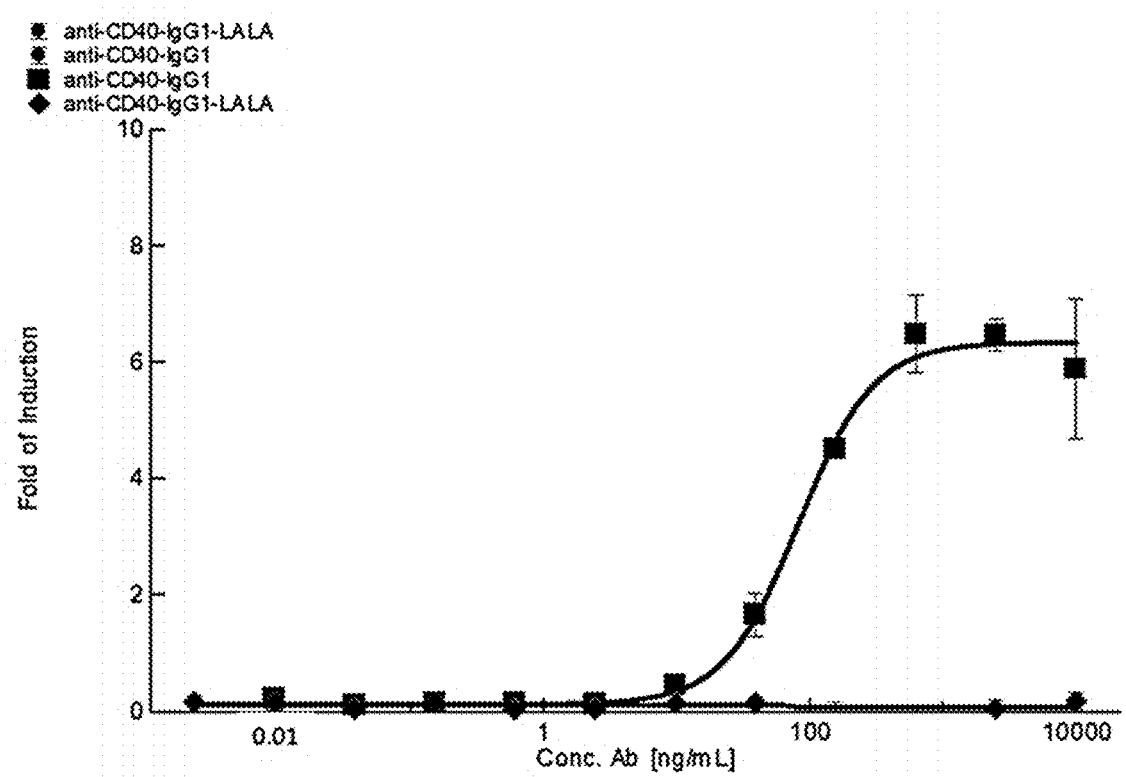

Example 15: Antibody-Mediated Effector Function of IgG1-LALA Anti CD40 Antibodies a. To test the potency of a LALA mutation in the constant part of an IgG1 antibody in diminishing antibody-mediated effector function, e.g. ADCC, a Jurkat effector cell reporter cell line based assay (Promega ADCC Bioassay, #G701A) has been applied according to manufacturer's instruction and using HEK-Blue-CD40L™ cells as target cells. 5000 HEK-Blue-CD40L™ cells were seeded per well in a white flat-bottom 384-well assay plate in 25 µl DMEM+10% FCS and incubated 20 h at 37° C., 5% $CO_2$. Medium was replaced with 8 µl RPMI medium containing 4% low-IgG FCS before 4000 effector cells per well were added in 8 µl of the same medium. Finally, CP-870,893 anti-CD40 antibodies, either containing an IgG1 or an IgG1-LALA Fc-part, were added in 8 µl medium at concentrations ranging from 10000 to 0.002 ng/ml. The plate was incubated for 6 h at 37° C., 5% $CO_2$. Effector cell luciferase activity was measured using BioGlo Luciferase assay reagents (Promega) according to the manufacturer's instructions. Luminescence was read using a Tecan M1000 microplate reader. Fold of induction was calculated with the formula RLU (antibody treatment−background)/RLU (vehicle−background). Fitting curves were obtained by using Excel (Microsoft) and XLfit (IDBS). FIG. 20 demonstrates that the LALA mutation in IgG1 abrogates Fc-receptor mediated signaling in effector cells.

Example 16: Safety of Agonistic Anti-CD40 Antibody Therapy in a Humanized Mouse Model a. To assess safety, a stem cell humanized mouse model was applied. Nod/Scid/gamma(c)(null) FcRg−/−mice lack mouse activating Fc-receptors. Therefore, Fc-receptor binding of therapeutic antibodies by human immune cells is not compromised by mouse Fc-receptor binding in this model. Mice were irradiated sub-lethal with 1.4 Gy within the first 24 hours after birth. After 4-6 hours mice were engrafted i.v. with 20000-50000 human hematopoietic stem cells isolated from cord blood. 12 weeks after engraftment the presence of human immune cells were validated by flow cytometry of peripheral blood cells. Successfully humanized mice were injected once i.v. with 3 µg/g CP-870,893, MAB-16-0451 or isotype control antibody. Body weight and temperature were measured before treatment and at different time points after antibody injection (FIG. 21). The data show a significant reduction in body temperature in 3 of 6 mice treated with CP-870,893 and these mice had to be sacrificed due to severe impairment of body conditions. In contrast, mice treated with MAB-16-0451 did not show significant effects on body temperature, neither there were any other overt signs of impaired body condition. This indicates that highly agonistic anti-CD40-IgG1-LALA antibodies lacking Fc-receptor binding activity, can be applied therapeutically without obvious signs of toxicity whereas toxic effects of the less active, agonistic CP-870,893-IgG2 antibody could be demonstrated in vivo in this model.

FIGURE LEGEND

FIG. 1: Cell Binding
The anti-CD40 IgG1-LALA monoclonal antibodies were tested for binding to cell-expressed CD40 antigen on HEK-Blue-CD40L™ cells (InvivoGen). EC50 values demonstrate potent binding of the tested antibodies.

FIG. 2: HEK-Blue EC50 Determination in 8-Point Analysis
The agonistic activity of humanized anti-CD40 IgG1-LALA monoclonal antibodies was tested in a cell-based NF-kB gene reporter assay. HEK-Blue-CD40L™ cells (InvivoGen) were incubated for 24 hours with different concentrations of the antibodies. EC50 values demonstrate the potency of the antibodies to induce NF-kB signaling.

FIG. 3: CD40-Ligand Epitope Competition
To test whether the humanized anti-CD40 IgG1-LALA monoclonal antibodies bind an epitope overlapping with the CD40L binding site, a CD40L competition ELISA was performed. Different concentrations of anti-CD40 antibodies were pre-incubated with CD40 recombinant protein to form a binding complex. Subsequently, the complex was added to microtiter plates coated with recombinant CD40L. After washing, bound CD40-anti-CD40 complexes were detected using a peroxidase-linked anti-human-F(ab)2 antibody. ELISA signals as for the reference CP-870,893 antibody indicate no competition with CD40L and thus binding to an epitope distinct from the CD40L binding site. The data demonstrates that the tested humanized anti-CD40 IgG1-LALA monoclonal antibodies bind to an epitope overlapping with the CD40L binding site.

FIG. 4: Cynomolgus Monkey-CD40 Binding Activity
Binding activity of the humanized anti-CD40 IgG1-LALA monoclonal antibodies to cynomolgus monkey (*Macaca fascicularis*) was tested in an ELISA using recombinant cynomolgus monkey CD40 recombinant protein (Acro Biosystems). EC50 values indicate potent binding of the antibodies. n.d.=not detectable in the tested concentration range FIG. 5a) b): Induction of Dendritic Cell Maturation
To test the agonistic activity of humanized anti-CD40 IgG1-LALA monoclonal antibodies on primary target cells, maturation of monocyte derived, immature dendritic cells was analyzed. Immature dendritic cells, which were differentiated in vitro from monocytes, were incubated for 48 h with agonistic anti-C40 antibodies at a concentration of 5 µg/ml. Dendritic cell derived, secreted IL12p40 was subsequently quantified in the medium supernatant by biochemical ELISA.

FIG. 6: Dendritic Cell Maturation

The activity of humanized anti-CD40 IgG1-LALA monoclonal antibodies to stimulate IL12p40 secretion by dendritic cells was determined at different antibody concentration and the activity was compared to CP-870,893 antibodies carrying different Fc-parts (IgG1, IgG1-LALA, IgG2 and IgG1-V11). Antibodies were incubated for 48 h with in vitro differentiated immature dendritic cells. IL12p40 release was measured by ELISA.

FIG. 7: EC50 determination of anti-CD40 antibodies in dendritic cell maturation The EC50 values of humanized anti-CD40 IgG1-LALA monoclonal antibodies in dendritic cell mediated IL12p40 secretion was determined by testing antibody concentrations ranging from 10-0.005 µg/ml. Antibodies were incubated for 48 h with in vitro differentiated immature dendritic cells. IL12p40 release was measured by ELISA.

FIG. 8: Cytokine Release Assay

Humanized anti-CD40 IgG1-LALA monoclonal antibodies were tested in high density PBMC cytokine release assay at 10 µg/ml to determine general induction of inflammatory cytokines such as TNF-alpha. The data indicates that in contrast to an anti-CD3 (OKT3) antibody the anti-CD40 antibodies do not induce significant TNF-alpha secretion.

FIG. 9: Antibody pulse chase cellular assay

Antibody binding dynamics and internalization was tested in a pulse chase cellular assay. Antibodies were incubated with HEK-Blue-CD40L™ cell cultures for 15 min at a concentration of 0.8 µg/ml. After washing, antibodies were allowed to internalize for 60 min before cells were washed again and remaining cell surface localized anti-CD0 antibody was detected by an Alexa-488 labelled secondary antibody. In conditions not allowing internalization, cells were treated similarly, but antibodies were incubated only for 15 min followed by washing and secondary antibody incubation. The data shows that in conditions allowing internalization, signals from surface localized antibodies are reduced to different extents for the tested humanized anti-CD40 IgG1-LALA monoclonal antibodies. Strong signal reduction is observed for all CP-870,893 antibody isoforms.

FIG. 10: Correlation of Gene Reporter Induction and Dendritic Cell Maturation Activity of Humanized Anti-CD40 Antibodies 88 humanized anti-CD40 IgG1-LALA antibodies were tested for their activity in a HEK-Blue gene reporter and a dendritic cell maturation assay. HEK-Blue gene reporter activity is quantified by OD@655 correlating to induced SEAP secretion, dendritic cell maturation is quantified by IL12p40 release (ELISA).

FIG. 11: Stimulation of Costimulatory Receptors on Dendritic Cells by Agonistic Anti-CD40 Antibodies In vitro differentiated immature iDCs were stimulated with agonistic CD40 antibodies, isotype control antibodies or CD40L for 48 hours. Expression of costimulatory receptor molecules was measured by flow cytometry. Mean fluorescence intensities were normalized to isotype control treatments or, in case of CD40L to untreated samples. Induction of expression is expressed as fold of induction (FOI) over control treatment.

FIG. 12: Cytokine Release by Anti-CD40 Treated Dendritic Cells

In vitro differentiated immature iDCs were stimulated with agonistic CD40 antibodies, isotype control antibodies or CD40L for 48 hours. Cytokine release was measured by ELISA (IL-12p40) or by flow cytometry using a BD cytometric bead array.

FIG. 13: Dose Dependent Stimulation of Costimulatory Receptors on Dendritic Cells by Agonistic Anti-CD40 Antibodies In vitro differentiated immature iDCs were stimulated with agonistic CD40 antibodies or isotype control antibodies for 48 hours at concentrations ranging from ranging from 10000 to 5 ng/ml. Expression of costimulatory receptor molecules was measured by flow cytometry. Mean fluorescence intensities were normalized to isotype control treatments. Induction of expression is expressed as fold of induction (FOI) over control treatment. Calculated EC50 values are presented in the table.

FIG. 14: Dose Dependent Cytokine Release by Anti-CD40 Treated Dendritic Cells In vitro differentiated immature iDCs were stimulated with agonistic CD40 antibodies and isotype control antibodies for 48 hours. Cytokine release was measured by flow cytometry using a BD cytometric bead array.

FIG. 15: Dose dependent stimulation of costimulatory receptors on B-cells by agonistic anti-CD40 antibodies B-cells were stimulated with agonistic CD40 antibodies or isotype control antibodies for 48 hours at concentrations ranging from ranging from 500 to 0.2 ng/ml. Expression of costimulatory receptor molecules was measured by flow cytometry. Mean fluorescence intensities were normalized to isotype control treatments. Induction of expression is expressed as fold of induction (FOI) over control treatment. Calculated EC50 values are presented in the table.

FIG. 16: Competition of anti-CD40 antibodies with CD40L binding to cell-expressed CD40

HEK-Blue-CD40L™ cells were preincubated with anti-CD40-IgG1-LALA antibodies at EC90 concentrations before CD40L was added in concentrations ranging from 10000 to 9.8 ng/ml. Anti-CD40 antibodies and CD40L binding to CD40 expressed on the cell surface were detected using different secondary, fluorophore-coupled antibodies.

FIG. 17: Induction of FasR (CD95) Death Receptor Expression by Agonistic CD40 Antibodies in Combination with CD40L Ramos B-lymphoma cells were stimulated over night with CD40L alone or in combination with agonistic anti-CD40 antibodies or isotype control antibodies. CD95 expression was quantified by flow cytometry, Upregulation of expression is expressed as fold of induction (FOI) over control treatment.

FIG. 18: Affinities of Humanized, Agonistic Anti-CD40 IgG1-LALA Antibodies

Biochemical affinities were measured by surface plasmon resonance on a Biacore T200 SPR instrument. Kinetic data were determined using a Langmuir 1:1 binding model.

FIG. 19: Antibody Competition on CD40 Binding

Binding of a preincubated mix of HIS-tagged CD40 protein and different anti-CD40 antibodies to plates coated with different anti-CD40 antibodies. Consecutive binding of both anti-CD40 antibodies are detected by anti-HIS POD-labelled antibodies.

FIG. 20: Antibody-mediated effector function of IgG1-LALA anti-CD40 antibodies Anti-CD40 antibody mediated effector function were analyzed using a Jurkat effector luciferase gene reporter cell line and HEK-Blue-CD40L™ as target cells. IgG1-LALA or IgG1 anti-CD40 antibodies were incubated in doses ranging from 10000 to 0.002 ng/ml with target and effector cells for 6 h. The fold of induction of measured luciferase activity indicates anti-CD40 antibody-mediated effector cell activation.

FIG. 21: Safety of Agonistic Anti-CD40 Antibody Therapy in a Humanized Mouse Model Nod/Scid/gamma(c)(null) FcRg−/−mice were injected with 3 µg/g MAB-16-0451 or CP-870,893 anti-CD40 antibodies on day 0. Temperature was measured before and at different time points after injection. Three mice treated with CP-870,893 which showed striking body temperature reduction had to be sacrificed after 3 days.

FIG. 22: Sequences (Amino Acids in One Letter Code)
Complete Sequences of Variable Regions (VR):
Heavy chain: VH complete: SEQ ID NO: 1-14
Light chain: VL complete: SEQ ID NO: 15-28
Complementary Determining Regions (CDR):
Heavy Chain: CDR-H1: SEQ ID NO: 29-42
CDR-H2: SEQ ID NO: 43-56
CDR-H3: SEQ ID NO: 57-70
Light Chain: CDR-L1: SEQ ID NO: 71-84
CDR-L2: SEQ ID NO: 85-98
CDR-L3: SEQ ID NO: 99-112

The invention claimed is:

1. An agonistic monoclonal antibody, or an antigen-binding fragment thereof, that specifically binds to the human CD40 receptor and is capable of inducing CD40 signaling independent of Fcγ mediated CD40 receptor cross-linking;
    wherein the antibody comprises a variable heavy (VH) region that is at least 85% identical to SEQ ID NO: 5 and comprises CDR regions CDR1H, CDR2H, and CDR3H as set forth in SEQ ID NO: 33, SEQ ID NO: 47, and SEQ ID NO: 61, respectively; and
    wherein the antibody comprises a variable light (VL) region that is at least 85% identical to SEQ ID NO: 19 and comprises CDR regions CDR1L, CDR2L, and CDR3L as set forth in SEQ ID NO: 75, SEQ ID NO: 89, and SEQ ID NO: 103, respectively.

2. The antibody according to claim 1, wherein the antibody is a humanized IgG1LALA antibody.

3. The antibody according to claim 2, wherein the antibody comprises at least amino acid substitutions at L234A and L235A of the human IgG1 Fc region according to the Kabat nomenclature.

4. The antibody or antigen-binding fragment thereof according to claim 1, wherein the antibody binds to an epitope that is overlapping with the CD40L binding site.

5. The antibody or antigen-binding fragment thereof according to claim 1, wherein the antibody activates human antigen presenting cells (APCs).

6. The antibody or antigen-binding fragment thereof according to claim 1, wherein the antibody activates cells selected from the group comprising dendritic cells (DCs), B-cells, monocytes, and myeloid cells.

7. The antibody or antigen-binding fragment thereof according to claim 1, wherein said antibody has an indirect immune cell-mediated cytotoxic effect on tumor cells.

8. The antibody or antigen-binding fragment thereof according to claim 1, which has at least one of the further characteristics
    (a) no binding to the Fcγ Receptor;
    (b) having a CD40 cell binding affinity with an EC50 value of equal to or less than 49.5 ng/ml;
    (c) having KD value of equal to or less than 15.7 nM;
    (d) being cross-reactive to cynomolgus monkey CD40 with a KD value equal to or less than 10.3 nM;
    (e) inhibiting CD40L by binding to CD40;
    (f) preventing synergistic and additive effects of CD40L-mediated functions;
    (g) inducing maturation of antigen presenting cells as determined by IL12p70 release with an EC50 value of equal or less than 208 ng/ml
    and/or as determined by the induction of CD86 on dendritic cells by at least 7.5-fold and with an EC50 of equal to or less than 148 ng/ml; and/or
    (h) reducing the level of CD40 on the cell surface by less than 50% of the reduction observed for CP-870,893.

9. A pharmaceutical composition comprising a pharmaceutically acceptable carrier and a therapeutically effective amount of the antibody or antigen-binding fragment thereof according to claim 1.

10. A method of treating cancer in a subject comprising administering to the subject an effective amount of the antibody or antigen-binding fragment thereof according to claim 1.

11. The method of treating a cancer according to claim 10, wherein the cancer is a solid tumor.

12. The method of treating a cancer according to claim 10, wherein, the cancer is selected from the group consisting of: pancreas cancer, including advanced pancreatic carcinoma, lung cancer, including non-small cell lung cancer and bronchioloalviolar cell lung cancer, bone cancer, skin cancer, including cutaneous melanoma, cancer of the head or neck, intraocular melanoma, ovarian cancer, rectal cancer, cancer of the anal region, gastric cancer, colon cancer, breast cancer, kidney cancer, Hodgkin's lymphoma, liver cancer, gallbladder cancer, bladder cancer, prostate cancer, thyroid cancer, salivary gland cancer, and uterine cancer.

13. The method of treating a cancer according to claim 10, wherein in combination with the antibody, the method further comprises administering a cytotoxic or cytostatic agent, or applying radiotherapy, including targeted radiotherapy, immunotherapy or surgery.

* * * * *

SEQUENCE LISTING

```
<160> NUMBER OF SEQ ID NOS: 112

<210> SEQ ID NO 1
<211> LENGTH: 122
<212> TYPE: PRT
<213> ORGANISM: Artificial Sequence
<220> FEATURE:
<223> OTHER INFORMATION: humanized antibody sequence

<400> SEQUENCE: 1

Glu Val Gln Leu Glu Glu Ser Gly Gly Asp Leu Val Gln Pro Gly Ala
1               5                   10                  15

Ser Leu Arg Leu Ser Cys Ala Ala Ser Gly Phe Ser Phe Ser Phe Ser
                20                  25                  30

Tyr Trp Ile Cys Trp Val Arg Gln Ala Pro Gly Lys Gly Leu Glu Leu
            35                  40                  45

Val Ser Cys Ile Tyr Thr Thr Ser Gly Ser Thr Tyr Tyr Ala Ser Trp
        50                  55                  60

Ala Lys Gly Arg Phe Thr Ile Ser Ile Asp Asn Ser Lys Thr Thr Leu
65                  70                  75                  80

Tyr Leu Gln Met Asn Ser Leu Arg Ala Glu Asp Thr Ala Thr Tyr Phe
                85                  90                  95

Cys Ala Arg Ser Ser Gly Val Ser Tyr Pro Ser Tyr Phe His Leu Trp
            100                 105                 110

Gly Gln Gly Thr Leu Val Thr Val Ser Ser
        115                 120

<210> SEQ ID NO 2
<211> LENGTH: 125
<212> TYPE: PRT
<213> ORGANISM: Artificial Sequence
<220> FEATURE:
<223> OTHER INFORMATION: humanized antibody sequence

<400> SEQUENCE: 2

Glu Val Gln Leu Glu Glu Ser Gly Gly Gly Leu Val Gln Pro Gly Ala
1               5                   10                  15

Ser Leu Arg Leu Ser Cys Ala Ala Ser Gly Phe Ser Phe Ser Gly Tyr
                20                  25                  30

Trp Met Cys Trp Val Arg Gln Ala Pro Gly Lys Gly Leu Glu Trp Val
            35                  40                  45

Gly Cys Ile Tyr Thr Asn Ser Gly Val Thr Tyr Tyr Ala Asn Trp Ala
        50                  55                  60

Lys Gly Arg Phe Thr Ile Ser Lys Asp Thr Ser Lys Thr Thr Leu Tyr
65                  70                  75                  80

Leu Gln Met Asn Ser Leu Arg Ala Glu Asp Thr Ala Thr Tyr Phe Cys
                85                  90                  95
```

Ala Arg Gly Gly Ala Ile Tyr Asn Asp Tyr Asp Tyr Ala Phe Tyr Tyr
            100                 105                 110

Ser Leu Trp Gly Gln Gly Thr Leu Val Thr Val Ser Ser
        115                 120                 125

<210> SEQ ID NO 3
<211> LENGTH: 117
<212> TYPE: PRT
<213> ORGANISM: Artificial Sequence
<220> FEATURE:
<223> OTHER INFORMATION: humanized antibody sequence

<400> SEQUENCE: 3

Glu Val Gln Leu Glu Glu Ser Gly Gly Asp Leu Val Gln Pro Gly Ala
1               5                   10                  15

Ser Leu Arg Leu Ser Cys Ala Ala Ser Gly Phe Asp Phe Asn Ser Asn
            20                  25                  30

Ala Met Ser Trp Val Arg Gln Ala Pro Gly Lys Gly Leu Glu Trp Val
        35                  40                  45

Ala Ser Ile Tyr Ala Gly Gly Ser Gly Ser Thr Tyr Tyr Ala Ser Trp
    50                  55                  60

Ala Lys Gly Arg Phe Thr Ile Ser Lys Asp Thr Ser Lys Thr Thr Leu
65                  70                  75                  80

Tyr Leu Gln Met Asn Ser Leu Arg Ala Glu Asp Thr Ala Thr Tyr Phe
                85                  90                  95

Cys Ala Arg Gly Ile Thr Arg Leu Pro Leu Trp Gly Gln Gly Thr Leu
            100                 105                 110

Val Thr Val Ser Ser
        115

<210> SEQ ID NO 4
<211> LENGTH: 117
<212> TYPE: PRT
<213> ORGANISM: Artificial Sequence
<220> FEATURE:
<223> OTHER INFORMATION: humanized antibody sequence

<400> SEQUENCE: 4

Glu Val Gln Leu Glu Glu Ser Gly Gly Asp Leu Val Gln Pro Gly Ala
1               5                   10                  15

Ser Leu Arg Leu Ser Cys Ala Val Ser Gly Phe Asp Phe Ser Ser Asn
            20                  25                  30

Ala Met Ser Trp Val Arg Gln Ala Pro Gly Lys Gly Leu Glu Trp Val
        35                  40                  45

Ser Ser Ile Tyr Ala Gly Ser Ser Gly Ser Thr Tyr Tyr Ala Ser Trp
    50                  55                  60

Ala Lys Gly Arg Phe Thr Ile Ser Lys Asp Ala Ser Lys Thr Thr Leu
65                  70                  75                  80

Tyr Leu Gln Met Asn Ser Leu Arg Ala Glu Asp Thr Ala Thr Tyr Phe
                85                  90                  95

Cys Ala Arg Gly Val Thr Arg Leu Pro Leu Trp Gly Gln Gly Thr Leu
            100                 105                 110

Val Thr Val Ser Ser
        115

<210> SEQ ID NO 5
<211> LENGTH: 117
<212> TYPE: PRT
<213> ORGANISM: Artificial Sequence
<220> FEATURE:
<223> OTHER INFORMATION: humanized antibody sequence

<400> SEQUENCE: 5

Glu Val Gln Leu Glu Glu Ser Gly Gly Gly Leu Val Gln Pro Gly Gly
1               5                   10                  15

Ser Leu Arg Leu Ser Cys Ala Ala Ser Gly Phe Asp Phe Ser Ser Asn
            20                  25                  30

Thr Met Cys Trp Val Arg Gln Ala Pro Gly Lys Gly Leu Glu Trp Val
        35                  40                  45

Ala Cys Ile Tyr Ala Gly Ser Ser Gly Ser Thr Tyr Tyr Ala Ser Trp
    50                  55                  60

Ala Lys Gly Arg Phe Thr Ile Ser Lys Asp Ile Ser Lys Thr Thr Leu
65                  70                  75                  80

Tyr Leu Gln Met Asn Ser Leu Arg Ala Glu Asp Thr Ala Thr Tyr Phe
                85                  90                  95

Cys Ala Arg Gly Leu Ser Arg Phe Ser Leu Trp Gly Gln Gly Thr Leu
            100                 105                 110

Val Thr Val Ser Ser
        115

<210> SEQ ID NO 6
<211> LENGTH: 117
<212> TYPE: PRT
<213> ORGANISM: Artificial Sequence
<220> FEATURE:
<223> OTHER INFORMATION: humanized antibody sequence

<400> SEQUENCE: 6

Glu Val Gln Leu Glu Glu Ser Gly Gly Gly Leu Val Gln Pro Gly Gly
1               5                   10                  15

Ser Leu Arg Leu Ser Cys Ala Ala Ser Gly Phe Asp Phe Ser Thr Asn
            20                  25                  30

Ala Val Ser Trp Val Arg Gln Ala Pro Gly Lys Gly Leu Glu Trp Val
        35                  40                  45

Gly Ser Ile Ser Ala Gly Ser Ser Gly Ser Thr Tyr Tyr Ala Ser Trp
    50                  55                  60

Ala Lys Gly Arg Phe Thr Ile Ser Lys Asp Thr Ser Lys Thr Thr Leu
65                  70                  75                  80

Tyr Leu Gln Met Asn Ser Leu Arg Ala Glu Asp Thr Ala Thr Tyr Phe
                85                  90                  95

Cys Ala Arg Gly Tyr Thr Tyr Leu Thr Leu Trp Gly Gln Gly Thr Leu
            100                 105                 110

Val Thr Val Ser Ser
        115

<210> SEQ ID NO 7
<211> LENGTH: 117
<212> TYPE: PRT
<213> ORGANISM: Artificial Sequence
<220> FEATURE:
<223> OTHER INFORMATION: humanized antibody sequence

<400> SEQUENCE: 7

Glu Val Gln Leu Glu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Asn
            20                  25                  30

```
Ala Met Ser Trp Val Arg Gln Ala Pro Gly Lys Gly Pro Glu Trp Val
            35                  40                  45

Val Thr Ile Tyr Ala Gly Ser Gly Ser Thr Tyr Tyr Ala Ser Trp
 50                  55                  60

Ala Lys Gly Arg Phe Thr Ile Ser Lys Asp Thr Ser Lys Thr Thr Leu
 65                  70                  75                  80

Tyr Leu Gln Met Asn Ser Leu Arg Ala Glu Asp Thr Ala Thr Tyr Phe
                85                  90                  95

Cys Ala Arg Gly Ala Thr Tyr Leu Thr Leu Trp Gly Gln Gly Thr Leu
                100                 105                 110

Val Thr Val Ser Ser
            115

<210> SEQ ID NO 8
<211> LENGTH: 117
<212> TYPE: PRT
<213> ORGANISM: Artificial Sequence
<220> FEATURE:
<223> OTHER INFORMATION: humanized antibody sequence

<400> SEQUENCE: 8

Glu Val Gln Leu Val Glu Ser Gly Gly Gly Leu Val Gln Pro Gly Gly
 1               5                   10                  15

Ser Leu Arg Leu Ser Cys Ala Ala Ser Gly Phe Asp Phe Ser Ser Asn
                20                  25                  30

Ala Met Ser Trp Val Arg Gln Ala Pro Gly Lys Gly Leu Glu Trp Val
            35                  40                  45

Gly Ile Ile Tyr Ala Gly Ser Ser Gly Ser Thr Tyr Tyr Ala Ser Trp
 50                  55                  60

Ala Lys Gly Arg Phe Thr Ile Ser Lys Asp Thr Ser Lys Thr Thr Leu
 65                  70                  75                  80

Tyr Leu Gln Met Asn Ser Leu Arg Ala Glu Asp Thr Ala Thr Tyr Phe
                85                  90                  95

Cys Ala Arg Gly Ala Thr Tyr Ile Thr Leu Trp Gly Gln Gly Thr Leu
                100                 105                 110

Val Thr Val Ser Ser
            115

<210> SEQ ID NO 9
<211> LENGTH: 117
<212> TYPE: PRT
<213> ORGANISM: Artificial Sequence
<220> FEATURE:
<223> OTHER INFORMATION: humanized antibody sequence

<400> SEQUENCE: 9

Glu Val Gln Leu Glu Glu Ser Gly Gly Gly Leu Val Gln Pro Gly Gly
 1               5                   10                  15

Ser Leu Arg Leu Ser Cys Ala Ala Ser Gly Phe Asp Phe Ser Ser Asn
                20                  25                  30

Ala Met Ser Trp Val Arg Gln Ala Pro Gly Lys Gly Leu Glu Trp Val
            35                  40                  45

Gly Thr Ile Tyr Ala Gly Ser Asn Gly Asn Thr Asp Tyr Ala Ser Trp
 50                  55                  60

Ala Lys Gly Arg Phe Thr Ile Ser Lys Asp Thr Ser Lys Thr Thr Leu
 65                  70                  75                  80

Tyr Leu Gln Met Asn Ser Leu Arg Ala Glu Asp Thr Ala Thr Tyr Phe
                85                  90                  95
```

Cys Ala Arg Gly Ala Ser Tyr Phe Thr Leu Trp Gly Gln Gly Thr Leu
                100                 105                 110

Val Thr Val Ser Ser
        115

<210> SEQ ID NO 10
<211> LENGTH: 117
<212> TYPE: PRT
<213> ORGANISM: Artificial Sequence
<220> FEATURE:
<223> OTHER INFORMATION: humanized antibody sequence

<400> SEQUENCE: 10

Glu Val Gln Leu Glu Glu Ser Gly Gly Gly Leu Val Gln Pro Gly Gly
1               5                   10                  15

Ser Leu Arg Leu Ser Cys Ala Ala Ser Gly Phe Asp Phe Ser Thr Asn
            20                  25                  30

Ala Met Cys Trp Val Arg Gln Ala Pro Gly Lys Gly Leu Glu Trp Val
        35                  40                  45

Ala Cys Ile Ala Ala Gly Ser Ser Ile Ile Thr Tyr Tyr Ala Ser Trp
    50                  55                  60

Ala Lys Gly Arg Phe Thr Ile Ser Lys Asp Thr Ser Lys Thr Thr Leu
65                  70                  75                  80

Tyr Leu Gln Met Asn Ser Leu Arg Ala Glu Asp Thr Ala Val Tyr Phe
                85                  90                  95

Cys Ala Arg Gly Leu Ser Arg Phe Ala Leu Trp Gly Gln Gly Thr Leu
                100                 105                 110

Val Thr Val Ser Ser
        115

<210> SEQ ID NO 11
<211> LENGTH: 123
<212> TYPE: PRT
<213> ORGANISM: Artificial Sequence
<220> FEATURE:
<223> OTHER INFORMATION: humanized antibody sequence

<400> SEQUENCE: 11

Glu Val Gln Leu Glu Glu Ser Gly Gly Gly Leu Val Gln Pro Gly Gly
1               5                   10                  15

Ser Leu Arg Leu Ser Cys Ala Ala Ser Gly Ile Asp Phe Ser Arg Tyr
            20                  25                  30

Tyr Tyr Met Cys Trp Val Arg Gln Ala Pro Gly Lys Gly Pro Glu Trp
        35                  40                  45

Val Ala Cys Tyr Ser Asn Gly Asp Gly Ser Thr Tyr Tyr Ala Ser Trp
    50                  55                  60

Ala Lys Gly Arg Phe Thr Ile Ser Lys Asp Thr Ser Lys Thr Thr Leu
65                  70                  75                  80

Tyr Leu Gln Met Asn Ser Leu Arg Ala Glu Asp Thr Ala Thr Tyr Phe
                85                  90                  95

Cys Ala Arg Gly Ala Asp Tyr Ser Ala Gly Ala Ala Ala Phe Asn Leu
                100                 105                 110

Trp Gly Gln Gly Thr Leu Val Thr Val Ser Ser
        115                 120

<210> SEQ ID NO 12
<211> LENGTH: 123
<212> TYPE: PRT

<213> ORGANISM: Artificial Sequence
<220> FEATURE:
<223> OTHER INFORMATION: humanized antibody sequence

<400> SEQUENCE: 12

Glu Val Gln Leu Glu Glu Ser Gly Gly Gly Leu Val Gln Pro Gly Gly
1               5                   10                  15

Ser Leu Arg Leu Ser Cys Ala Ala Ser Gly Ile Asp Phe Ser Arg Tyr
            20                  25                  30

Tyr Tyr Ile Cys Trp Val Arg Gln Ala Pro Gly Lys Gly Pro Glu Trp
        35                  40                  45

Val Ala Cys Phe Ala Asn Gly Asp Gly Ser Thr Tyr Tyr Ala Ser Trp
    50                  55                  60

Ala Lys Gly Arg Phe Thr Ile Ser Lys Asp Thr Ser Lys Thr Thr Leu
65                  70                  75                  80

Tyr Leu Gln Met Asn Ser Leu Arg Ala Glu Asp Thr Ala Thr Tyr Phe
                85                  90                  95

Cys Ala Arg Gly Ala Asp Tyr Ser Gly Gly Ala Ala Phe Asn Leu
            100                 105                 110

Trp Gly Gln Gly Thr Leu Val Thr Val Ser Ser
        115                 120

<210> SEQ ID NO 13
<211> LENGTH: 126
<212> TYPE: PRT
<213> ORGANISM: Artificial Sequence
<220> FEATURE:
<223> OTHER INFORMATION: humanized antibody sequence

<400> SEQUENCE: 13

Glu Val Gln Leu Glu Glu Ser Gly Gly Gly Leu Val Gln Pro Gly Gly
1               5                   10                  15

Ser Leu Arg Leu Ser Cys Ala Ala Ser Gly Ile Asp Phe Ser Arg Tyr
            20                  25                  30

Phe Tyr Met Cys Trp Val Arg Gln Ala Pro Gly Lys Gly Leu Glu Trp
        35                  40                  45

Val Ala Cys Ile Gly Pro Gly Val Ser Gly Asp Thr Tyr Tyr Ala Ser
    50                  55                  60

Trp Ala Lys Gly Arg Phe Thr Ile Ser Gly Asp Thr Ser Lys Thr Thr
65                  70                  75                  80

Leu Tyr Leu Gln Met Asn Ser Leu Arg Ala Glu Asp Thr Ala Thr Tyr
                85                  90                  95

Phe Cys Ala Arg Gly Val Asp Tyr Thr Tyr Gly Asp Ala Gly Ala Ala
            100                 105                 110

Phe Asn Leu Trp Gly Gln Gly Thr Leu Val Thr Val Ser Ser
        115                 120                 125

<210> SEQ ID NO 14
<211> LENGTH: 125
<212> TYPE: PRT
<213> ORGANISM: Artificial Sequence
<220> FEATURE:
<223> OTHER INFORMATION: humanized antibody sequence

<400> SEQUENCE: 14

Glu Val Gln Leu Glu Glu Ser Gly Gly Gly Leu Val Gln Pro Gly Ala
1               5                   10                  15

Ser Leu Arg Leu Ser Cys Ala Ala Ser Gly Ile Asp Phe Ser Arg Tyr
            20                  25                  30

Phe Tyr Val Cys Trp Val Arg Gln Ala Pro Gly Lys Gly Leu Glu Trp
            35                  40                  45

Val Gly Cys Phe Ala Asn His Asp Asp Ser Ile Tyr Tyr Ala Gly Trp
 50                  55                  60

Met Asn Gly Arg Phe Thr Ile Ser Lys Asp Thr Ser Lys Thr Thr Leu
 65                  70                  75                  80

Tyr Leu Gln Met Asn Ser Leu Arg Ala Glu Asp Thr Ala Thr Tyr Phe
                 85                  90                  95

Cys Ala Arg Gly Val Asp Tyr Val Gly Tyr Gly Ala Ala Phe
                100                 105                 110

Asn Leu Trp Gly Gln Gly Thr Leu Val Thr Val Ser Ser
            115                 120                 125

<210> SEQ ID NO 15
<211> LENGTH: 112
<212> TYPE: PRT
<213> ORGANISM: Artificial Sequence
<220> FEATURE:
<223> OTHER INFORMATION: humanized antibody sequence

<400> SEQUENCE: 15

Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Ser Ile Ser Ser Tyr
             20                  25                  30

Leu Ala Trp Tyr Gln Gln Lys Pro Gly Gln Ala Pro Lys Leu Leu Ile
         35                  40                  45

Tyr Ser Ala Ser Lys Leu Pro Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr His Cys Gln Thr Tyr Tyr Tyr Ser Ser Ser
                 85                  90                  95

Ser Ser Tyr Asp Tyr Gly Phe Gly Gln Gly Thr Lys Val Val Ile Lys
                100                 105                 110

<210> SEQ ID NO 16
<211> LENGTH: 111
<212> TYPE: PRT
<213> ORGANISM: Artificial Sequence
<220> FEATURE:
<223> OTHER INFORMATION: humanized antibody sequence

<400> SEQUENCE: 16

Asp Ile Val Met Thr Gln Ser Pro Ser Ser Leu Ser Ala Ser Val Gly
 1               5                  10                  15

Asp Arg Val Thr Ile Thr Cys Gln Ala Ser Gln Ser Ile Ser Ser Tyr
             20                  25                  30

Leu Ala Trp Tyr Gln Gln Lys Pro Gly Gln Ala Pro Lys Leu Leu Ile
         35                  40                  45

Tyr Lys Ala Ser Thr Leu Ala Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Ser Tyr Tyr Gly Ser Ser Ser
                 85                  90                  95

Ile Ser Tyr Asn Ala Phe Gly Gln Gly Thr Lys Val Val Ile Lys

<210> SEQ ID NO 17
<211> LENGTH: 110
<212> TYPE: PRT
<213> ORGANISM: Artificial Sequence
<220> FEATURE:
<223> OTHER INFORMATION: humanized antibody sequence

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Ser Tyr
            20                  25                  30

Leu Ala Trp Tyr Gln Gln Lys Pro Gly Gln Ala Pro Lys Leu Leu Ile
        35                  40                  45

Tyr Asp Ala Ser Lys Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gly Thr Tyr Tyr Gly Ser Thr
                85                  90                  95

Thr Ile Ser Ala Phe Gly Gln Gly Thr Lys Val Val Ile Lys
            100                 105                 110

<210> SEQ ID NO 18
<211> LENGTH: 110
<212> TYPE: PRT
<213> ORGANISM: Artificial Sequence
<220> FEATURE:
<223> OTHER INFORMATION: humanized antibody sequence

<400> SEQUENCE: 18

Asp Ile Val Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Ser Tyr
            20                  25                  30

Leu Ala Trp Tyr Gln Gln Lys Pro Gly Gln Ala Pro Lys Leu Leu Ile
        35                  40                  45

Tyr Asp Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gly Thr Val Tyr Gly Ser Ser
                85                  90                  95

Thr Ile Ser Ala Phe Gly Gln Gly Thr Lys Val Val Ile Lys
            100                 105                 110

<210> SEQ ID NO 19
<211> LENGTH: 111
<212> TYPE: PRT
<213> ORGANISM: Artificial Sequence
<220> FEATURE:
<223> OTHER INFORMATION: humanized antibody sequence

<400> SEQUENCE: 19

Asp Ile Val Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Asn Tyr
            20                  25                  30

Leu Ala Trp Tyr Gln Gln Lys Pro Gly Gln Ala Pro Lys Leu Leu Ile
            35                  40                  45

Tyr Asp Ala Ser Lys Leu Ala Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gly Asp Tyr Tyr Gly Ser
                85                  90                  95

Ser Tyr Val Val Ala Phe Gly Gly Gly Thr Lys Val Val Ile Lys
                100                 105                 110

<210> SEQ ID NO 20
<211> LENGTH: 111
<212> TYPE: PRT
<213> ORGANISM: Artificial Sequence
<220> FEATURE:
<223> OTHER INFORMATION: humanized antibody sequence

<400> SEQUENCE: 20

Asp Ile Val Met Thr Gln Ser Pro Ser Ser Leu Ser Ala Ser Val Gly
1               5                   10                  15

Asp Arg Val Thr Ile Thr Cys Gln Ala Ser His Ser Ile Ser Ser Thr
            20                  25                  30

Tyr Leu Ser Trp Tyr Gln Gln Lys Pro Gly Gln Ala Pro Lys Leu Leu
        35                  40                  45

Ile Tyr Arg Ala Ser Thr Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Tyr Thr Asp Tyr Gly Ser
                85                  90                  95

Ser Tyr Val Ser Thr Phe Gly Gln Gly Thr Lys Val Val Ile Lys
                100                 105                 110

<210> SEQ ID NO 21
<211> LENGTH: 112
<212> TYPE: PRT
<213> ORGANISM: Artificial Sequence
<220> FEATURE:
<223> OTHER INFORMATION: humanized antibody sequence

<400> SEQUENCE: 21

Asp Ile Val Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Asn Tyr
            20                  25                  30

Leu Ser Trp Tyr Gln Gln Lys Pro Gly Gln Ala Pro Lys Leu Leu Ile
        35                  40                  45

Tyr Arg Ala Ser Thr Leu Pro Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gly Tyr Tyr Ser Gly Thr
                85                  90                  95

Thr Tyr Asp Ser Thr Ala Phe Gly Gln Gly Thr Lys Val Val Ile Lys
                100                 105                 110

```
<210> SEQ ID NO 22
<211> LENGTH: 114
<212> TYPE: PRT
<213> ORGANISM: Artificial Sequence
<220> FEATURE:
<223> OTHER INFORMATION: humanized antibody sequence

<400> SEQUENCE: 22

Asp Ile Val Met Thr Gln Ser Pro Ser Ser Leu Ser Ala Ser Val Gly
1               5                   10                  15

Asp Arg Val Thr Ile Thr Cys Gln Ala Ser Gln Ser Ile Gly Ser Tyr
            20                  25                  30

Leu Ala Trp Tyr Gln Gln Lys Pro Gly Gln Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gly Tyr Tyr Ser Thr Thr Thr
                85                  90                  95

Thr Thr Thr Tyr Asp Ser Ser Ala Phe Gly Gln Gly Thr Lys Val Val
            100                 105                 110

Ile Lys

<210> SEQ ID NO 23
<211> LENGTH: 112
<212> TYPE: PRT
<213> ORGANISM: Artificial Sequence
<220> FEATURE:
<223> OTHER INFORMATION: humanized antibody sequence

<400> SEQUENCE: 23

Asp Ile Val Met Thr Gln Ser Pro Ser Ser Leu Ser Ala Ser Val Gly
1               5                   10                  15

Asp Arg Val Thr Ile Thr Cys Gln Ala Ser Glu Ser Val Val Ser Asn
            20                  25                  30

Asn Arg Leu Ala Trp Tyr Gln Gln Lys Pro Gly Gln Ala Pro Lys Leu
        35                  40                  45

Leu Ile Tyr Leu Ala Ser Thr Leu Pro Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Ala Gly Tyr Lys Ser Ser
                85                  90                  95

Ser Thr Asp Gly Thr Ala Phe Gly Gln Gly Thr Lys Val Val Ile Lys
            100                 105                 110

<210> SEQ ID NO 24
<211> LENGTH: 111
<212> TYPE: PRT
<213> ORGANISM: Artificial Sequence
<220> FEATURE:
<223> OTHER INFORMATION: humanized antibody sequence

<400> SEQUENCE: 24

Asp Ile Val Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Ser Tyr
            20                  25                  30
```

```
Leu Ser Trp Tyr Gln Gln Lys Pro Gly Gln Ala Pro Lys Leu Leu Ile
            35                  40                  45

Tyr Leu Thr Ser Thr Leu Ala Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gly Tyr Tyr Ser Ser Ser
                 85                  90                  95

Tyr Val Ser Asn Gly Phe Gly Gln Gly Thr Lys Val Val Ile Lys
                100                 105                 110
```

<210> SEQ ID NO 25
<211> LENGTH: 110
<212> TYPE: PRT
<213> ORGANISM: Artificial Sequence
<220> FEATURE:
<223> OTHER INFORMATION: humanized antibody sequence

<400> SEQUENCE: 25

```
Asp Ile Gln Met Thr Gln Ser Pro Ser Ser Leu Ser Ala Ser Val Gly
 1               5                  10                  15

Asp Arg Val Thr Ile Thr Cys Gln Ala Ser Glu Ser Ile Gly Asn Ala
                 20                  25                  30

Leu Val Trp Tyr Gln Gln Lys Pro Gly Gln Ala Pro Lys Leu Leu Ile
            35                  40                  45

Tyr Arg Ala Ser Ile Leu Ala Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Asp Tyr Tyr Gly Ser Ser Thr
                 85                  90                  95

Glu Tyr Asn Thr Phe Gly Gln Gly Thr Lys Val Val Ile Lys
                100                 105                 110
```

<210> SEQ ID NO 26
<211> LENGTH: 110
<212> TYPE: PRT
<213> ORGANISM: Artificial Sequence
<220> FEATURE:
<223> OTHER INFORMATION: humanized antibody sequence

<400> SEQUENCE: 26

```
Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Ser Ile Ser Ser Arg
                 20                  25                  30

Leu Ala Trp Tyr Gln Gln Lys Pro Gly Gln Ala Pro Lys Leu Leu Ile
            35                  40                  45

Tyr Arg Ala Ser Thr Leu Ala Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Asp Tyr Tyr Gly Ser Ser Thr
                 85                  90                  95

Glu Tyr Asn Ala Phe Gly Gln Gly Thr Lys Val Val Ile Lys
                100                 105                 110
```

<210> SEQ ID NO 27

```
<211> LENGTH: 114
<212> TYPE: PRT
<213> ORGANISM: Artificial Sequence
<220> FEATURE:
<223> OTHER INFORMATION: humanized antibody sequence

<400> SEQUENCE: 27

Asp Ile Val Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Ser Tyr
            20                  25                  30

Leu Ala Trp Tyr Gln Gln Lys Pro Gly Gln Ala Pro Lys Leu Leu Ile
        35                  40                  45

Tyr Arg Ala Ser Ile Leu Ala Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Thr Tyr Tyr Ser Ser Arg Thr
                85                  90                  95

Tyr Ser Tyr Gly Ser Pro Asn Ala Phe Gly Gln Gly Thr Lys Val Val
            100                 105                 110

Ile Lys

<210> SEQ ID NO 28
<211> LENGTH: 109
<212> TYPE: PRT
<213> ORGANISM: Artificial Sequence
<220> FEATURE:
<223> OTHER INFORMATION: humanized antibody sequence

<400> SEQUENCE: 28

Asp Ile Val Met Thr Gln Ser Pro Ser Ser Leu Ser Ala Ser Val Gly
1               5                   10                  15

Asp Arg Val Thr Ile Thr Cys Gln Ala Ser Gln Ser Ile Gly Ser Tyr
            20                  25                  30

Leu Ser Trp Tyr Gln Gln Lys Pro Gly Gln Ala Pro Lys Leu Leu Ile
        35                  40                  45

Tyr Arg Ala Thr Thr Leu Ala Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Tyr Tyr Arg Asp Ser Ser
                85                  90                  95

Ser Ser Ala Phe Gly Gln Gly Thr Lys Val Val Ile Lys
            100                 105

<210> SEQ ID NO 29
<211> LENGTH: 6
<212> TYPE: PRT
<213> ORGANISM: Artificial Sequence
<220> FEATURE:
<223> OTHER INFORMATION: CDR

<400> SEQUENCE: 29

Phe Ser Tyr Trp Ile Cys
1               5

<210> SEQ ID NO 30
<211> LENGTH: 5
<212> TYPE: PRT
```

```
<213> ORGANISM: Artificial Sequence
<220> FEATURE:
<223> OTHER INFORMATION: CDR

<400> SEQUENCE: 30

Gly Tyr Trp Met Cys
1               5

<210> SEQ ID NO 31
<211> LENGTH: 5
<212> TYPE: PRT
<213> ORGANISM: Artificial Sequence
<220> FEATURE:
<223> OTHER INFORMATION: humanized antibody sequence

<400> SEQUENCE: 31

Ser Asn Ala Met Ser
1               5

<210> SEQ ID NO 32
<211> LENGTH: 5
<212> TYPE: PRT
<213> ORGANISM: Artificial Sequence
<220> FEATURE:
<223> OTHER INFORMATION: humanized antibody sequence

<400> SEQUENCE: 32

Ser Asn Ala Met Ser
1               5

<210> SEQ ID NO 33
<211> LENGTH: 5
<212> TYPE: PRT
<213> ORGANISM: Artificial Sequence
<220> FEATURE:
<223> OTHER INFORMATION: humanized antibody sequences

<400> SEQUENCE: 33

Ser Asn Thr Met Cys
1               5

<210> SEQ ID NO 34
<211> LENGTH: 5
<212> TYPE: PRT
<213> ORGANISM: Artificial Sequence
<220> FEATURE:
<223> OTHER INFORMATION: humanized antibody sequence

<400> SEQUENCE: 34

Thr Asn Ala Val Ser
1               5

<210> SEQ ID NO 35
<211> LENGTH: 5
<212> TYPE: PRT
<213> ORGANISM: Artificial Sequence
<220> FEATURE:
<223> OTHER INFORMATION: humanized antibody sequence

<400> SEQUENCE: 35

Ser Asn Ala Met Ser
1               5

<210> SEQ ID NO 36
<211> LENGTH: 5
<212> TYPE: PRT
<213> ORGANISM: Artificial Sequence
```

```
<220> FEATURE:
<223> OTHER INFORMATION: humanized antibody sequence

<400> SEQUENCE: 36

Ser Asn Ala Met Ser
1               5

<210> SEQ ID NO 37
<211> LENGTH: 5
<212> TYPE: PRT
<213> ORGANISM: Artificial Sequence
<220> FEATURE:
<223> OTHER INFORMATION: humanized antibody sequence

<400> SEQUENCE: 37

Ser Asn Ala Met Ser
1               5

<210> SEQ ID NO 38
<211> LENGTH: 5
<212> TYPE: PRT
<213> ORGANISM: Artificial Sequence
<220> FEATURE:
<223> OTHER INFORMATION: humanized antibody sequence

<400> SEQUENCE: 38

Thr Asn Ala Met Cys
1               5

<210> SEQ ID NO 39
<211> LENGTH: 6
<212> TYPE: PRT
<213> ORGANISM: Artificial Sequence
<220> FEATURE:
<223> OTHER INFORMATION: humanized antibody sequence

<400> SEQUENCE: 39

Arg Tyr Tyr Tyr Met Cys
1               5

<210> SEQ ID NO 40
<211> LENGTH: 6
<212> TYPE: PRT
<213> ORGANISM: Artificial Sequence
<220> FEATURE:
<223> OTHER INFORMATION: humanized antibody sequence

<400> SEQUENCE: 40

Arg Tyr Tyr Tyr Ile Cys
1               5

<210> SEQ ID NO 41
<211> LENGTH: 6
<212> TYPE: PRT
<213> ORGANISM: Artificial Sequence
<220> FEATURE:
<223> OTHER INFORMATION: humanized antibody sequence

<400> SEQUENCE: 41

Arg Tyr Phe Tyr Met Cys
1               5

<210> SEQ ID NO 42
<211> LENGTH: 6
<212> TYPE: PRT
<213> ORGANISM: Artificial Sequence
<220> FEATURE:
```

<223> OTHER INFORMATION: humanized antibody sequence

<400> SEQUENCE: 42

Arg Tyr Phe Tyr Val Cys
1               5

<210> SEQ ID NO 43
<211> LENGTH: 17
<212> TYPE: PRT
<213> ORGANISM: Artificial Sequence
<220> FEATURE:
<223> OTHER INFORMATION: humanized antibody sequence

<400> SEQUENCE: 43

Cys Ile Tyr Thr Thr Ser Gly Ser Thr Tyr Tyr Ala Ser Trp Ala Lys
1               5                   10                  15

Gly

<210> SEQ ID NO 44
<211> LENGTH: 17
<212> TYPE: PRT
<213> ORGANISM: Artificial Sequence
<220> FEATURE:
<223> OTHER INFORMATION: humanized antibody sequence

<400> SEQUENCE: 44

Cys Ile Tyr Thr Asn Ser Gly Val Thr Tyr Tyr Ala Asn Trp Ala Lys
1               5                   10                  15

Gly

<210> SEQ ID NO 45
<211> LENGTH: 18
<212> TYPE: PRT
<213> ORGANISM: Artificial Sequence
<220> FEATURE:
<223> OTHER INFORMATION: humanized antibody sequence

<400> SEQUENCE: 45

Ser Ile Tyr Ala Gly Gly Ser Gly Ser Thr Tyr Tyr Ala Ser Trp Ala
1               5                   10                  15

Lys Gly

<210> SEQ ID NO 46
<211> LENGTH: 18
<212> TYPE: PRT
<213> ORGANISM: Artificial Sequence
<220> FEATURE:
<223> OTHER INFORMATION: humanized antibody sequence

<400> SEQUENCE: 46

Ser Ile Tyr Ala Gly Ser Ser Gly Ser Thr Tyr Tyr Ala Ser Trp Ala
1               5                   10                  15

Lys Gly

<210> SEQ ID NO 47
<211> LENGTH: 18
<212> TYPE: PRT
<213> ORGANISM: Artificial Sequence
<220> FEATURE:
<223> OTHER INFORMATION: humanized antibody sequence

<400> SEQUENCE: 47

Cys Ile Tyr Ala Gly Ser Ser Gly Ser Thr Tyr Tyr Ala Ser Trp Ala
1               5                   10                  15

Lys Gly

<210> SEQ ID NO 48
<211> LENGTH: 18
<212> TYPE: PRT
<213> ORGANISM: Artificial Sequence
<220> FEATURE:
<223> OTHER INFORMATION: humanized antibody sequence

<400> SEQUENCE: 48

Ser Ile Ser Ala Gly Ser Ser Gly Ser Thr Tyr Tyr Ala Ser Trp Ala
1               5                   10                  15

Lys Gly

<210> SEQ ID NO 49
<211> LENGTH: 18
<212> TYPE: PRT
<213> ORGANISM: Artificial Sequence
<220> FEATURE:
<223> OTHER INFORMATION: humanized antibody sequence

<400> SEQUENCE: 49

Thr Ile Tyr Ala Gly Ser Ser Gly Ser Thr Tyr Tyr Ala Ser Trp Ala
1               5                   10                  15

Lys Gly

<210> SEQ ID NO 50
<211> LENGTH: 18
<212> TYPE: PRT
<213> ORGANISM: Artificial Sequence
<220> FEATURE:
<223> OTHER INFORMATION: humanized antibody sequence

<400> SEQUENCE: 50

Ile Ile Tyr Ala Gly Ser Ser Gly Ser Thr Tyr Tyr Ala Ser Trp Ala
1               5                   10                  15

Lys Gly

<210> SEQ ID NO 51
<211> LENGTH: 18
<212> TYPE: PRT
<213> ORGANISM: Artificial Sequence
<220> FEATURE:
<223> OTHER INFORMATION: humanized antibody sequence

<400> SEQUENCE: 51

Thr Ile Tyr Ala Gly Ser Asn Gly Asn Thr Asp Tyr Ala Ser Trp Ala
1               5                   10                  15

Lys Gly

<210> SEQ ID NO 52
<211> LENGTH: 18
<212> TYPE: PRT
<213> ORGANISM: Artificial Sequence
<220> FEATURE:
<223> OTHER INFORMATION: humanized antibody sequence

<400> SEQUENCE: 52

Cys Ile Ala Ala Gly Ser Ser Ile Ile Thr Tyr Tyr Ala Ser Trp Ala
1               5                   10                  15

Lys Gly

```
<210> SEQ ID NO 53
<211> LENGTH: 17
<212> TYPE: PRT
<213> ORGANISM: Artificial Sequence
<220> FEATURE:
<223> OTHER INFORMATION: humanized antibody sequence

<400> SEQUENCE: 53

Cys Tyr Ser Asn Gly Asp Gly Ser Thr Tyr Tyr Ala Ser Trp Ala Lys
1               5                   10                  15
Gly

<210> SEQ ID NO 54
<211> LENGTH: 17
<212> TYPE: PRT
<213> ORGANISM: Artificial Sequence
<220> FEATURE:
<223> OTHER INFORMATION: humanized antibody sequence

<400> SEQUENCE: 54

Cys Phe Ala Asn Gly Asp Gly Ser Thr Tyr Tyr Ala Ser Trp Ala Lys
1               5                   10                  15
Gly

<210> SEQ ID NO 55
<211> LENGTH: 18
<212> TYPE: PRT
<213> ORGANISM: Artificial Sequence
<220> FEATURE:
<223> OTHER INFORMATION: humanized antibody sequence

<400> SEQUENCE: 55

Cys Ile Gly Pro Gly Val Ser Gly Asp Thr Tyr Tyr Ala Ser Trp Ala
1               5                   10                  15
Lys Gly

<210> SEQ ID NO 56
<211> LENGTH: 17
<212> TYPE: PRT
<213> ORGANISM: Artificial Sequence
<220> FEATURE:
<223> OTHER INFORMATION: humanized antibody sequence

<400> SEQUENCE: 56

Cys Phe Ala Asn His Asp Asp Ser Ile Tyr Tyr Ala Gly Trp Met Asn
1               5                   10                  15
Gly

<210> SEQ ID NO 57
<211> LENGTH: 12
<212> TYPE: PRT
<213> ORGANISM: Artificial Sequence
<220> FEATURE:
<223> OTHER INFORMATION: humanized antibody sequence

<400> SEQUENCE: 57

Ser Ser Gly Val Ser Tyr Pro Ser Tyr Phe His Leu
1               5                   10

<210> SEQ ID NO 58
<211> LENGTH: 16
<212> TYPE: PRT
<213> ORGANISM: Artificial Sequence
<220> FEATURE:
<223> OTHER INFORMATION: humanized antibody sequence
```

```
<400> SEQUENCE: 58

Gly Gly Ala Ile Tyr Asn Asp Tyr Asp Tyr Ala Phe Tyr Tyr Ser Leu
1               5                   10                  15

<210> SEQ ID NO 59
<211> LENGTH: 7
<212> TYPE: PRT
<213> ORGANISM: Artificial Sequence
<220> FEATURE:
<223> OTHER INFORMATION: humanized antibody sequence

<400> SEQUENCE: 59

Gly Ile Thr Arg Leu Pro Leu
1               5

<210> SEQ ID NO 60
<211> LENGTH: 7
<212> TYPE: PRT
<213> ORGANISM: Artificial Sequence
<220> FEATURE:
<223> OTHER INFORMATION: humanized antibody sequence

<400> SEQUENCE: 60

Gly Val Thr Arg Leu Pro Leu
1               5

<210> SEQ ID NO 61
<211> LENGTH: 7
<212> TYPE: PRT
<213> ORGANISM: Artificial Sequence
<220> FEATURE:
<223> OTHER INFORMATION: humanized antibody sequence

<400> SEQUENCE: 61

Gly Leu Ser Arg Phe Ser Leu
1               5

<210> SEQ ID NO 62
<211> LENGTH: 7
<212> TYPE: PRT
<213> ORGANISM: Artificial Sequence
<220> FEATURE:
<223> OTHER INFORMATION: humanized antibody sequence

<400> SEQUENCE: 62

Gly Tyr Thr Tyr Leu Thr Leu
1               5

<210> SEQ ID NO 63
<211> LENGTH: 7
<212> TYPE: PRT
<213> ORGANISM: Artificial Sequence
<220> FEATURE:
<223> OTHER INFORMATION: humanized antibody sequence

<400> SEQUENCE: 63

Gly Ala Thr Tyr Leu Thr Leu
1               5

<210> SEQ ID NO 64
<211> LENGTH: 7
<212> TYPE: PRT
<213> ORGANISM: Artificial Sequence
<220> FEATURE:
<223> OTHER INFORMATION: humanized antibody sequence
```

```
<400> SEQUENCE: 64

Gly Ala Thr Tyr Ile Thr Leu
1               5

<210> SEQ ID NO 65
<211> LENGTH: 7
<212> TYPE: PRT
<213> ORGANISM: Artificial Sequence
<220> FEATURE:
<223> OTHER INFORMATION: humanized antibody sequence

<400> SEQUENCE: 65

Gly Ala Ser Tyr Phe Thr Leu
1               5

<210> SEQ ID NO 66
<211> LENGTH: 7
<212> TYPE: PRT
<213> ORGANISM: Artificial Sequence
<220> FEATURE:
<223> OTHER INFORMATION: humanized antibody sequence

<400> SEQUENCE: 66

Gly Leu Ser Arg Phe Ala Leu
1               5

<210> SEQ ID NO 67
<211> LENGTH: 13
<212> TYPE: PRT
<213> ORGANISM: Artificial Sequence
<220> FEATURE:
<223> OTHER INFORMATION: humanized antibody sequence

<400> SEQUENCE: 67

Gly Ala Asp Tyr Ser Ala Gly Ala Ala Ala Phe Asn Leu
1               5                   10

<210> SEQ ID NO 68
<211> LENGTH: 13
<212> TYPE: PRT
<213> ORGANISM: Artificial Sequence
<220> FEATURE:
<223> OTHER INFORMATION: humanized antibody sequence

<400> SEQUENCE: 68

Gly Ala Asp Tyr Ser Gly Gly Ala Ala Ala Phe Asn Leu
1               5                   10

<210> SEQ ID NO 69
<211> LENGTH: 15
<212> TYPE: PRT
<213> ORGANISM: Artificial Sequence
<220> FEATURE:
<223> OTHER INFORMATION: humanized antibody sequence

<400> SEQUENCE: 69

Gly Val Asp Tyr Thr Tyr Gly Asp Ala Gly Ala Ala Phe Asn Leu
1               5                   10                  15

<210> SEQ ID NO 70
<211> LENGTH: 15
<212> TYPE: PRT
<213> ORGANISM: Artificial Sequence
<220> FEATURE:
<223> OTHER INFORMATION: humanized antibody sequence

<400> SEQUENCE: 70
```

```
Gly Val Asp Tyr Thr Val Gly Tyr Gly Gly Ala Ala Phe Asn Leu
1               5                   10                  15

<210> SEQ ID NO 71
<211> LENGTH: 11
<212> TYPE: PRT
<213> ORGANISM: Artificial Sequence
<220> FEATURE:
<223> OTHER INFORMATION: humanized antibody sequence

<400> SEQUENCE: 71

Gln Ala Ser Gln Ser Ile Ser Ser Tyr Leu Ala
1               5                   10

<210> SEQ ID NO 72
<211> LENGTH: 11
<212> TYPE: PRT
<213> ORGANISM: Artificial Sequence
<220> FEATURE:
<223> OTHER INFORMATION: humanized antibody sequence

<400> SEQUENCE: 72

Gln Ala Ser Gln Ser Ile Ser Ser Tyr Leu Ala
1               5                   10

<210> SEQ ID NO 73
<211> LENGTH: 11
<212> TYPE: PRT
<213> ORGANISM: Artificial Sequence
<220> FEATURE:
<223> OTHER INFORMATION: humanized antibody sequence

<400> SEQUENCE: 73

Gln Ala Ser Gln Ser Ile Ser Ser Tyr Leu Ala
1               5                   10

<210> SEQ ID NO 74
<211> LENGTH: 11
<212> TYPE: PRT
<213> ORGANISM: Artificial Sequence
<220> FEATURE:
<223> OTHER INFORMATION: humanized antibody sequence

<400> SEQUENCE: 74

Gln Ala Ser Gln Ser Ile Ser Ser Tyr Leu Ala
1               5                   10

<210> SEQ ID NO 75
<211> LENGTH: 11
<212> TYPE: PRT
<213> ORGANISM: Artificial Sequence
<220> FEATURE:
<223> OTHER INFORMATION: humanized antibody sequence

<400> SEQUENCE: 75

Gln Ala Ser Gln Ser Ile Ser Asn Tyr Leu Ala
1               5                   10

<210> SEQ ID NO 76
<211> LENGTH: 12
<212> TYPE: PRT
<213> ORGANISM: Artificial Sequence
<220> FEATURE:
<223> OTHER INFORMATION: humanized antibody sequence

<400> SEQUENCE: 76
```

Gln Ala Ser His Ser Ile Ser Ser Thr Tyr Leu Ser
1               5                   10

<210> SEQ ID NO 77
<211> LENGTH: 11
<212> TYPE: PRT
<213> ORGANISM: Artificial Sequence
<220> FEATURE:
<223> OTHER INFORMATION: humanized antibody sequence

<400> SEQUENCE: 77

Gln Ala Ser Gln Ser Ile Ser Asn Tyr Leu Ser
1               5                   10

<210> SEQ ID NO 78
<211> LENGTH: 11
<212> TYPE: PRT
<213> ORGANISM: Artificial Sequence
<220> FEATURE:
<223> OTHER INFORMATION: humanized antibody sequence

<400> SEQUENCE: 78

Gln Ala Ser Gln Ser Ile Gly Ser Tyr Leu Ala
1               5                   10

<210> SEQ ID NO 79
<211> LENGTH: 13
<212> TYPE: PRT
<213> ORGANISM: Artificial Sequence
<220> FEATURE:
<223> OTHER INFORMATION: humanized antibody sequence

<400> SEQUENCE: 79

Gln Ala Ser Glu Ser Val Val Ser Asn Asn Arg Leu Ala
1               5                   10

<210> SEQ ID NO 80
<211> LENGTH: 11
<212> TYPE: PRT
<213> ORGANISM: Artificial Sequence
<220> FEATURE:
<223> OTHER INFORMATION: humanized antibody sequence

<400> SEQUENCE: 80

Gln Ala Ser Gln Ser Ile Ser Ser Tyr Leu Ser
1               5                   10

<210> SEQ ID NO 81
<211> LENGTH: 11
<212> TYPE: PRT
<213> ORGANISM: Artificial Sequence
<220> FEATURE:
<223> OTHER INFORMATION: humanized antibody sequence

<400> SEQUENCE: 81

Gln Ala Ser Glu Ser Ile Gly Asn Ala Leu Val
1               5                   10

<210> SEQ ID NO 82
<211> LENGTH: 11
<212> TYPE: PRT
<213> ORGANISM: Artificial Sequence
<220> FEATURE:
<223> OTHER INFORMATION: humanized antibody sequence

<400> SEQUENCE: 82

Gln Ala Ser Gln Ser Ile Ser Ser Arg Leu Ala

<210> SEQ ID NO 83
<211> LENGTH: 11
<212> TYPE: PRT
<213> ORGANISM: Artificial Sequence
<220> FEATURE:
<223> OTHER INFORMATION: humanized antibody sequence

<400> SEQUENCE: 83

Gln Ala Ser Gln Ser Ile Ser Ser Tyr Leu Ala
1               5                   10

<210> SEQ ID NO 84
<211> LENGTH: 11
<212> TYPE: PRT
<213> ORGANISM: Artificial Sequence
<220> FEATURE:
<223> OTHER INFORMATION: humanized antibody sequence

<400> SEQUENCE: 84

Gln Ala Ser Gln Ser Ile Gly Ser Tyr Leu Ser
1               5                   10

<210> SEQ ID NO 85
<211> LENGTH: 7
<212> TYPE: PRT
<213> ORGANISM: Artificial Sequence
<220> FEATURE:
<223> OTHER INFORMATION: humanized antibody sequence

<400> SEQUENCE: 85

Ser Ala Ser Lys Leu Pro Ser
1               5

<210> SEQ ID NO 86
<211> LENGTH: 7
<212> TYPE: PRT
<213> ORGANISM: Artificial Sequence
<220> FEATURE:
<223> OTHER INFORMATION: humanized antibody sequence

<400> SEQUENCE: 86

Lys Ala Ser Thr Leu Ala Ser
1               5

<210> SEQ ID NO 87
<211> LENGTH: 7
<212> TYPE: PRT
<213> ORGANISM: Artificial Sequence
<220> FEATURE:
<223> OTHER INFORMATION: humanized antibody sequence

<400> SEQUENCE: 87

Asp Ala Ser Lys Leu Ala Ser
1               5

<210> SEQ ID NO 88
<211> LENGTH: 7
<212> TYPE: PRT
<213> ORGANISM: Artificial Sequence
<220> FEATURE:
<223> OTHER INFORMATION: humanized antibody sequence

<400> SEQUENCE: 88

Asp Ala Ser Thr Leu Ala Ser
1               5

```
<210> SEQ ID NO 89
<211> LENGTH: 7
<212> TYPE: PRT
<213> ORGANISM: Artificial Sequence
<220> FEATURE:
<223> OTHER INFORMATION: humanized antibody sequence

<400> SEQUENCE: 89

Asp Ala Ser Lys Leu Ala Ser
1               5

<210> SEQ ID NO 90
<211> LENGTH: 7
<212> TYPE: PRT
<213> ORGANISM: Artificial Sequence
<220> FEATURE:
<223> OTHER INFORMATION: humanized antibody sequence

<400> SEQUENCE: 90

Arg Ala Ser Thr Leu Ala Ser
1               5

<210> SEQ ID NO 91
<211> LENGTH: 7
<212> TYPE: PRT
<213> ORGANISM: Artificial Sequence
<220> FEATURE:
<223> OTHER INFORMATION: humanized antibody sequence

<400> SEQUENCE: 91

Arg Ala Ser Thr Leu Pro Ser
1               5

<210> SEQ ID NO 92
<211> LENGTH: 7
<212> TYPE: PRT
<213> ORGANISM: Artificial Sequence
<220> FEATURE:
<223> OTHER INFORMATION: humanized antibody sequence

<400> SEQUENCE: 92

Arg Ala Ser Thr Leu Ala Ser
1               5

<210> SEQ ID NO 93
<211> LENGTH: 7
<212> TYPE: PRT
<213> ORGANISM: Artificial Sequence
<220> FEATURE:
<223> OTHER INFORMATION: humanized antibody sequence

<400> SEQUENCE: 93

Leu Ala Ser Thr Leu Pro Ser
1               5

<210> SEQ ID NO 94
<211> LENGTH: 7
<212> TYPE: PRT
<213> ORGANISM: Artificial Sequence
<220> FEATURE:
<223> OTHER INFORMATION: humanized antibody sequence

<400> SEQUENCE: 94

Leu Thr Ser Thr Leu Ala Ser
1               5
```

<210> SEQ ID NO 95
<211> LENGTH: 7
<212> TYPE: PRT
<213> ORGANISM: Artificial Sequence
<220> FEATURE:
<223> OTHER INFORMATION: humanized antibody sequence

<400> SEQUENCE: 95

Arg Ala Ser Ile Leu Ala Ser
1               5

<210> SEQ ID NO 96
<211> LENGTH: 7
<212> TYPE: PRT
<213> ORGANISM: Artificial Sequence
<220> FEATURE:
<223> OTHER INFORMATION: humanized antibody sequence

<400> SEQUENCE: 96

Arg Ala Ser Thr Leu Ala Ser
1               5

<210> SEQ ID NO 97
<211> LENGTH: 7
<212> TYPE: PRT
<213> ORGANISM: Artificial Sequence
<220> FEATURE:
<223> OTHER INFORMATION: humanized antibody sequence

<400> SEQUENCE: 97

Arg Ala Ser Ile Leu Ala Ser
1               5

<210> SEQ ID NO 98
<211> LENGTH: 7
<212> TYPE: PRT
<213> ORGANISM: Artificial Sequence
<220> FEATURE:
<223> OTHER INFORMATION: humanized antibody sequence

<400> SEQUENCE: 98

Arg Ala Thr Thr Leu Ala Ser
1               5

<210> SEQ ID NO 99
<211> LENGTH: 14
<212> TYPE: PRT
<213> ORGANISM: Artificial Sequence
<220> FEATURE:
<223> OTHER INFORMATION: humanized antibody sequence

<400> SEQUENCE: 99

Gln Thr Tyr Tyr Tyr Ser Ser Ser Ser Ser Tyr Asp Tyr Gly
1               5                   10

<210> SEQ ID NO 100
<211> LENGTH: 13
<212> TYPE: PRT
<213> ORGANISM: Artificial Sequence
<220> FEATURE:
<223> OTHER INFORMATION: humanized antibody sequence

<400> SEQUENCE: 100

Gln Ser Tyr Tyr Gly Ser Ser Ser Ile Ser Tyr Asn Ala
1               5                   10

```
<210> SEQ ID NO 101
<211> LENGTH: 12
<212> TYPE: PRT
<213> ORGANISM: Artificial Sequence
<220> FEATURE:
<223> OTHER INFORMATION: humanized antibody sequence

<400> SEQUENCE: 101

Gln Gly Thr Tyr Tyr Gly Ser Thr Thr Ile Ser Ala
1               5                   10

<210> SEQ ID NO 102
<211> LENGTH: 12
<212> TYPE: PRT
<213> ORGANISM: Artificial Sequence
<220> FEATURE:
<223> OTHER INFORMATION: humanized antibody sequence

<400> SEQUENCE: 102

Gln Gly Thr Val Tyr Gly Ser Ser Thr Ile Ser Ala
1               5                   10

<210> SEQ ID NO 103
<211> LENGTH: 13
<212> TYPE: PRT
<213> ORGANISM: Artificial Sequence
<220> FEATURE:
<223> OTHER INFORMATION: humanized antibody sequence

<400> SEQUENCE: 103

Gln Gly Gly Asp Tyr Tyr Gly Ser Ser Tyr Val Val Ala
1               5                   10

<210> SEQ ID NO 104
<211> LENGTH: 12
<212> TYPE: PRT
<213> ORGANISM: Artificial Sequence
<220> FEATURE:
<223> OTHER INFORMATION: humanized antibody sequence

<400> SEQUENCE: 104

Gln Tyr Thr Asp Tyr Gly Ser Ser Tyr Val Ser Thr
1               5                   10

<210> SEQ ID NO 105
<211> LENGTH: 14
<212> TYPE: PRT
<213> ORGANISM: Artificial Sequence
<220> FEATURE:
<223> OTHER INFORMATION: humanized antibody sequence

<400> SEQUENCE: 105

Gln Gly Tyr Tyr Tyr Ser Gly Thr Thr Tyr Asp Ser Thr Ala
1               5                   10

<210> SEQ ID NO 106
<211> LENGTH: 16
<212> TYPE: PRT
<213> ORGANISM: Artificial Sequence
<220> FEATURE:
<223> OTHER INFORMATION: humanized antibody sequence

<400> SEQUENCE: 106

Gln Gly Tyr Tyr Tyr Ser Thr Thr Thr Thr Tyr Asp Ser Ser Ala
1               5                   10                  15

<210> SEQ ID NO 107
```

```
<211> LENGTH: 12
<212> TYPE: PRT
<213> ORGANISM: Artificial Sequence
<220> FEATURE:
<223> OTHER INFORMATION: humanized antibody sequence

<400> SEQUENCE: 107

Ala Gly Tyr Lys Ser Ser Ser Thr Asp Gly Thr Ala
1               5                   10

<210> SEQ ID NO 108
<211> LENGTH: 13
<212> TYPE: PRT
<213> ORGANISM: Artificial Sequence
<220> FEATURE:
<223> OTHER INFORMATION: humanized antibody sequence

<400> SEQUENCE: 108

Gln Gly Tyr Tyr Ser Ser Ser Ser Tyr Val Ser Asn Gly
1               5                   10

<210> SEQ ID NO 109
<211> LENGTH: 12
<212> TYPE: PRT
<213> ORGANISM: Artificial Sequence
<220> FEATURE:
<223> OTHER INFORMATION: humanized antibody sequence

<400> SEQUENCE: 109

Gln Asp Tyr Tyr Gly Ser Ser Thr Glu Tyr Asn Thr
1               5                   10

<210> SEQ ID NO 110
<211> LENGTH: 12
<212> TYPE: PRT
<213> ORGANISM: Artificial Sequence
<220> FEATURE:
<223> OTHER INFORMATION: humanized antibody sequence

<400> SEQUENCE: 110

Gln Asp Tyr Tyr Gly Ser Ser Thr Glu Tyr Asn Ala
1               5                   10

<210> SEQ ID NO 111
<211> LENGTH: 16
<212> TYPE: PRT
<213> ORGANISM: Artificial Sequence
<220> FEATURE:
<223> OTHER INFORMATION: humanized antibody sequence

<400> SEQUENCE: 111

Gln Thr Tyr Tyr Ser Ser Arg Thr Tyr Ser Tyr Gly Ser Pro Asn Ala
1               5                   10                  15

<210> SEQ ID NO 112
<211> LENGTH: 11
<212> TYPE: PRT
<213> ORGANISM: Artificial Sequence
<220> FEATURE:
<223> OTHER INFORMATION: CDR

<400> SEQUENCE: 112

Gln Ser Tyr Tyr Arg Asp Ser Ser Ser Ser Ala
1               5                   10
```